(12) United States Patent
Andreev et al.

(10) Patent No.: US 7,409,298 B2
(45) Date of Patent: Aug. 5, 2008

(54) MATCHED FILTRATION WITH EXPERIMENTAL NOISE DETERMINATION FOR DENOISING, PEAK PICKING AND QUANTITATION IN LC-MS

(75) Inventors: Victor P. Andreev, Coconut Grove, FL (US); Tomas Rejtar, Somerville, MA (US); Barry L. Karger, Newton, MA (US)

(73) Assignee: Northeastern University, Boston, MA (US)

( * ) Notice: Subject to any disclaimer, the term of this patent is extended or adjusted under 35 U.S.C. 154(b) by 421 days.

(21) Appl. No.: 10/510,992

(22) PCT Filed: Apr. 11, 2003

(86) PCT No.: PCT/US03/11193

§ 371 (c)(1),
(2), (4) Date: Jul. 11, 2005

(87) PCT Pub. No.: WO03/087770

PCT Pub. Date: Oct. 23, 2003

(65) Prior Publication Data

US 2005/0261838 A1    Nov. 24, 2005

Related U.S. Application Data

(60) Provisional application No. 60/440,950, filed on Jan. 17, 2003, provisional application No. 60/372,155, filed on Apr. 12, 2002.

(51) Int. Cl.
*G01N 31/00* (2006.01)
(52) U.S. Cl. .................................................. 702/23
(58) Field of Classification Search ................. 702/23
See application file for complete search history.

(56) References Cited

U.S. PATENT DOCUMENTS

| | | | |
|---|---|---|---|
| 5,668,373 A | 9/1997 | Robbat, Jr. et al. | 250/339.12 |
| 5,862,512 A * | 1/1999 | Voorhees et al. | 702/2 |
| 5,995,989 A | 11/1999 | Gedcke et al. | 708/300 |
| 6,449,584 B1 * | 9/2002 | Bertrand et al. | 702/180 |
| 6,873,915 B2 * | 3/2005 | Hastings | 702/22 |
| 2002/0063208 A1 * | 5/2002 | Hastings | 250/281 |
| 2006/0036425 A1 * | 2/2006 | Le Cocq et al. | 703/22 |
| 2008/0059079 A1 * | 3/2008 | Watabe et al. | 702/23 |

* cited by examiner

*Primary Examiner*—John E Barlow, Jr.
*Assistant Examiner*—Aditya S Bhat
(74) *Attorney, Agent, or Firm*—Weingarten, Schurgin, Gagnebin & Lebovici LLP

(57) ABSTRACT

An improved system and method of analyzing sample data that increases the reliability of peak (compound) detection and identification in the presence of chemical and/or random noise. The sample analysis system includes a compound-separating unit for separating constituent compounds in a sample mixture, a compound-analyzing unit for identifying and quantitating at least one of the separated compounds, and a computer for acquiring data from the compound-separating and compound-analyzing units, for generating a multi-dimensional data set incorporating the acquired data, for executing an algorithm for reducing noise in the data set and for detecting peaks (compounds) in the noise-reduced data set, and for identifying/quantitating the detected compounds.

32 Claims, 12 Drawing Sheets

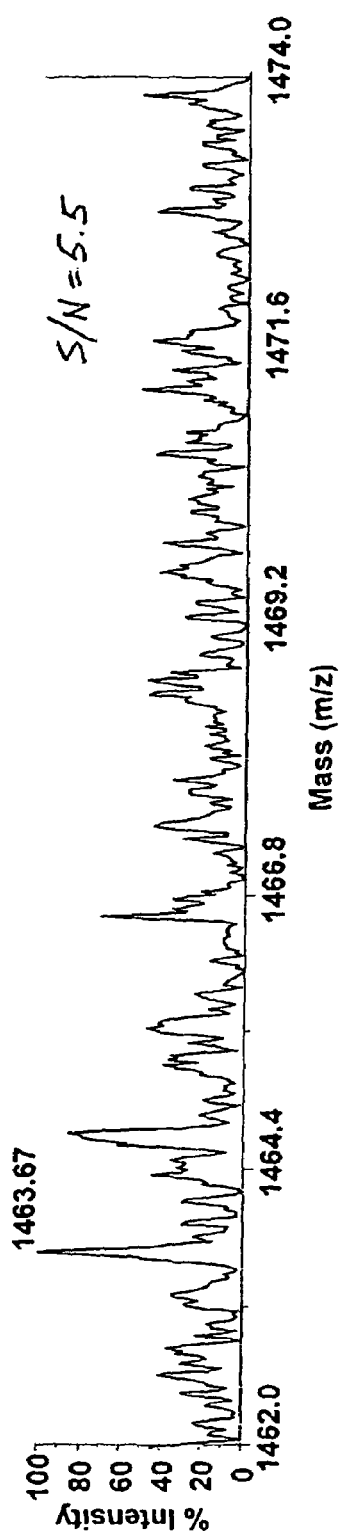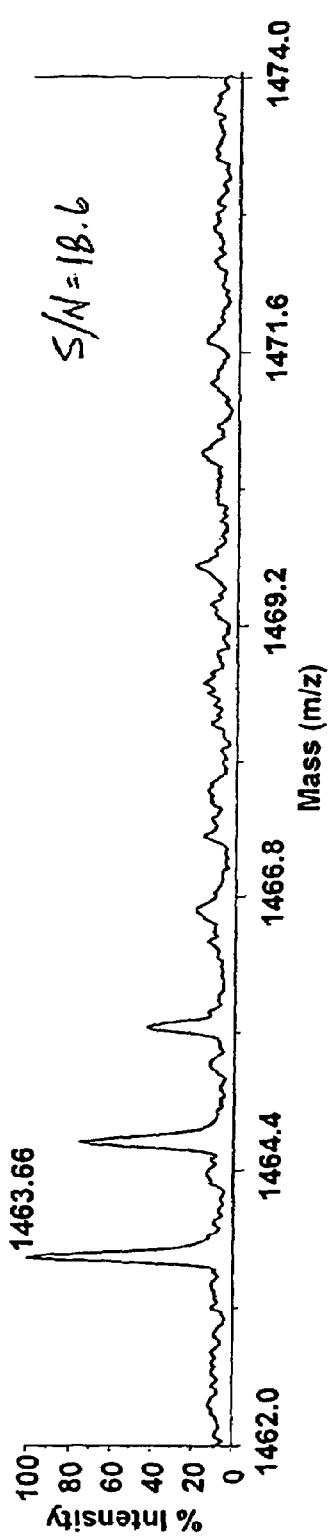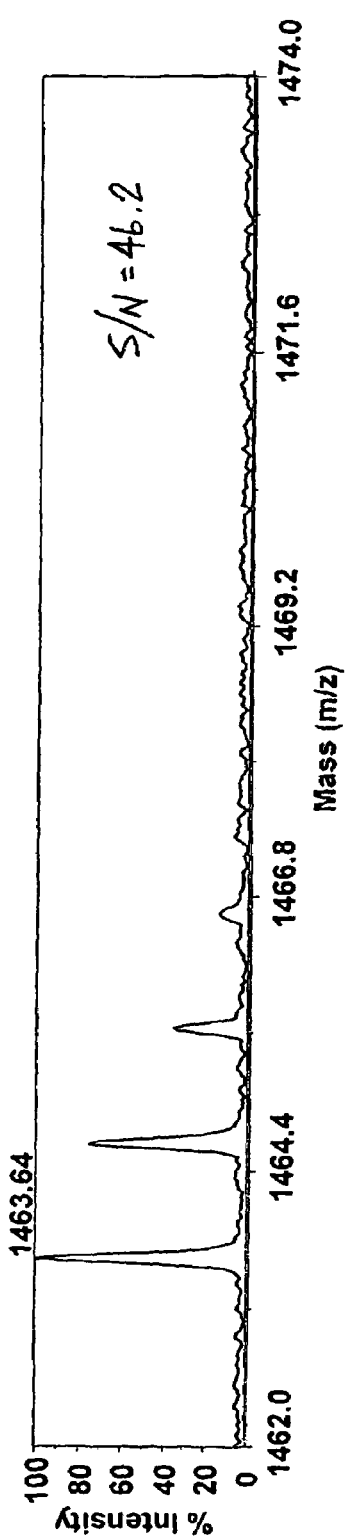
Fig. 4a
Fig. 4b
Fig. 4c

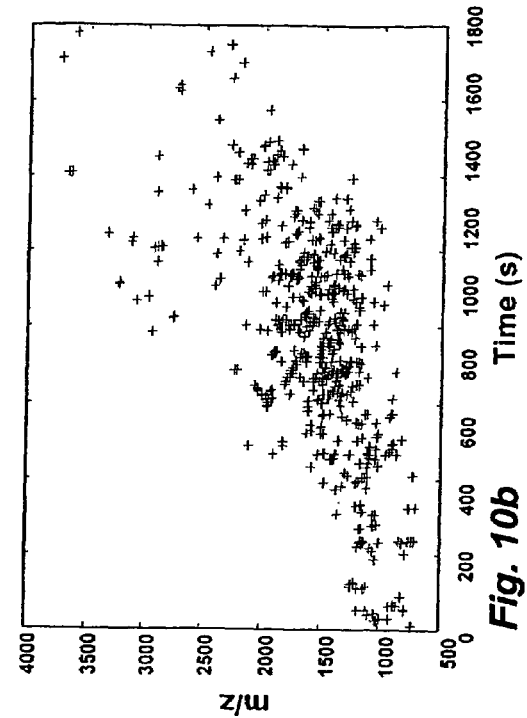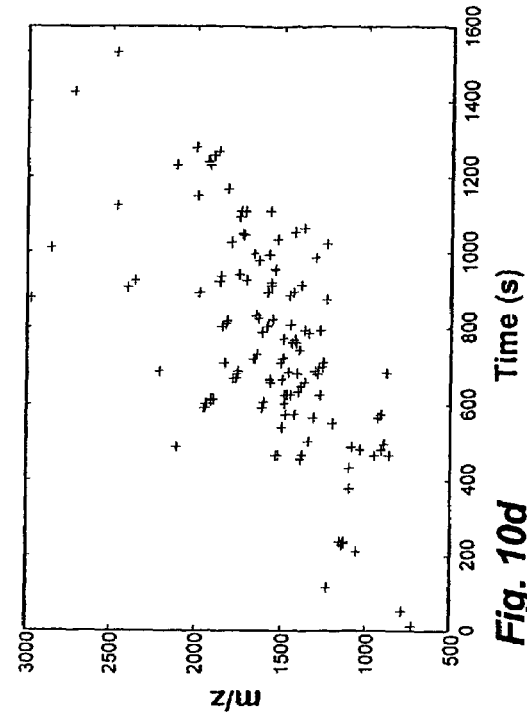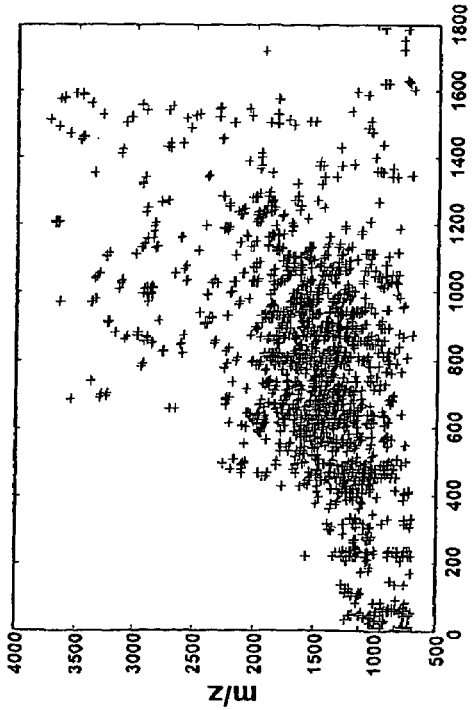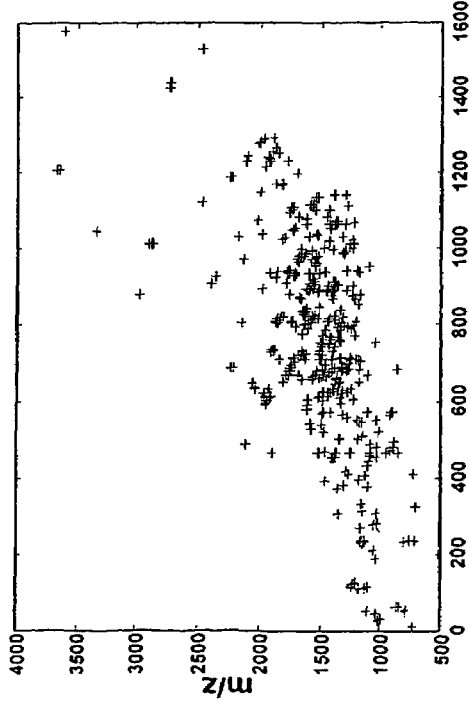
Fig. 10a
Fig. 10b
Fig. 10c
Fig. 10d

MATCHED FILTRATION WITH EXPERIMENTAL NOISE DETERMINATION FOR DENOISING, PEAK PICKING AND QUANTITATION IN LC-MS

CROSS REFERENCE TO RELATED APPLICATIONS

This application claims priority of U.S. Provisional Patent Application No. 60/372,155 filed Apr. 12, 2002 entitled PEAK PICKING ALGORITHM FOR LC-MS, and U.S. Provisional Patent Application No. 60/440,950 filed Jan. 17, 2003 entitled MATCHED FILTRATION WITH EXPERIMENTAL NOISE DETERMINATION FOR DENOISING, PEAK PICKING AND QUANTITATION IN LC-MS.

STATEMENT REGARDING FEDERALLY SPONSORED RESEARCH OR DEVELOPMENT

N/A

BACKGROUND OF THE INVENTION

The present application relates generally to chemical analysis, and more specifically to a system and method of analyzing a multi-dimensional data set having a first dimension corresponding to compound separation and a second dimension corresponding to compound spectra for characterizing compounds present in a sample mixture.

Sample analysis techniques are known that may be employed for identifying and quantitating one or more compounds present in a sample mixture. For purposes of illustration, a conventional system for performing such sample analysis includes a compound-separating unit for chromatographically or electrophoretically separating constituent compounds in a mixture, and a compound-identifying unit such as a mass spectrometer for identifying and quantitating one or more of the separated compounds. The spectrometrical detector typically represents the separated compounds in a chromatogram or an electropherogram as respective peaks with associated elution times. The mass spectrometer typically provides molecular masses-to-charge (m/z) of the compounds ions for the respective peaks to aid in identifying and quantitating the constituent compounds in the mixture.

One drawback of conventional systems for analyzing sample mixtures is that the analysis of data generated by the system often creates a limitation, especially when data generated from complex sample mixtures are analyzed. Another drawback of conventional sample analysis techniques is that noise in the data frequently makes the detection and identification of peaks, particularly, low intensity peaks, less reliable. Such noise may comprise chemical noise and/or random noise having a magnitude high enough to reduce significantly the peak Signal-to-Noise ratio (S/N), thereby making the detection of low intensity peaks problematic.

For example, a peak picking algorithm (the CODA algorithm) is known in which a mass chromatographic quality index (MSQ) is calculated as the inner product of an extracted ion chromatogram and its smoothed and mean-subtracted version. The higher the Signal-to-Noise ratio (S/N) in the initial chromatogram, the more it is like its smoothed version and the higher the MSQ. Only chromatograms with high MSQ are selected and combined to produce the Total Ion Chromatogram (TIC) with reduced noise and background. The CODA algorithm provides a peak selection technique in which only m/z values corresponding to an MSQ value greater than a predetermined threshold are selected. However, the CODA algorithm is not using the a priori information about the shape and width of chromatographic and MS peaks and is typically not robust to chemical and random noise.

The application of Sequential Paired Covariance (SPC) to the "de-noising" of CE-ESI-TOF data is also known. Electropherograms are reconstructed by considering the intensity of the signal equal to the covariance of two adjacent spectra. The correlation of the two adjacent spectra is employed as a measure of their similarity. Further, noise that is uncorrelated between successive spectra is suppressed. However, such denoising during SPC can significantly alter the data. For example, information related to the position of peaks in the m/z dimension may be lost, and therefore the spectra may have to be re-analyzed.

Moreover, a Windowed Mass Selection Method (WMSM) is known in which a width for the window in the chromatographic dimension is specified (in terms of the number of spectra N) from the analysis of extracted ion chromatograms. For each extracted ion chromatogram, its mean value is calculated and subtracted, so that in the resultant function the chromatographic peaks are positive, while the noise may be both positive and negative. For each m/z value and for each spectrum, the product of N values of signal intensities (for the given value of m/z) is calculated. If there is at least one zero value inside the specified window, then the product is equal to zero. Accordingly, noisy regions are set to zero in the resultant signal matrix. A second window, typically much wider than the first window, is also specified, and the product of signal intensities inside this window is calculated. If the product for the second window is not equal to zero, then the resultant signal intensity is set to be zero. Peaks are thus eliminated that are much wider than the expected chromatographic peak. However, the WMSM technique is generally not very robust to the non-uniformities connected with limited ion statistics. For example, one missing data point (e.g., a negative spike) in a good chromatographic peak may eliminate this peak from the resultant signal.

It would therefore be desirable to have an improved system and method of analyzing sample data for characterizing compounds in a sample mixture. Such an improved system and method would avoid the drawbacks of the above-described conventional sample analysis techniques.

BRIEF SUMMARY OF THE INVENTION

In accordance with the present invention, an improved system and method of analyzing a multi-dimensional data set is provided that increases the reliability of peak detection and identification in the presence of chemical and/or random noise. The system and method of the present invention achieves such increased reliability by (1) generating a multi-dimensional data set having a first dimension corresponding to compound separation information and a second dimension corresponding to compound characteristic information, e.g., spectral information, (2) reducing noise in the multi-dimensional data set, (3) detecting peak candidates in the first dimension of the data set, and (4) identifying peaks from among the detected peak candidates in the second dimension of the data set.

In one embodiment, a sample analysis system includes a compound-separating unit configured to separate constituent compounds in a sample mixture (e.g., liquid chromatography, gas chromatography, thin layer chromatography, capillary electrophoresis, or slab gel electrophoresis), and a compound-analyzing unit configured to identify and to quantitate at least one of the separated compounds. The sample analysis system further includes at least one computer operative to acquire data from the compound-separating and compound-analyzing units, to generate a multi-dimensional data set incorporating the acquired data, to execute at least one algorithm for reducing noise in the data set and for detecting peaks (i.e., compounds) in the noise-reduced data set, and to identify/quantitate the detected compounds.

In a preferred embodiment of the invention, the compound-separating unit is configured to generate Liquid Chromatography (LC) data, and the compound-analyzing unit is configured to generate Mass Spectrometry (MS) data. Further, the computer is operative to acquire MS data from the compound-analyzing unit, and to generate a multi-dimensional LC-MS data set represented by an LC-MS data array having a chromatographic time dimension and a mass spectral dimension. Next, the computer executes the noise reducing and peak detecting algorithm as follows.

First, the LC-MS data array is analyzed in the chromatographic time dimension to generate one or more first extracted ion chromatograms having one or more regions in which there are no peaks conforming to predetermined chromatographic criteria ("chromatographic peaks"). The chromatographic peak-free regions of the first extracted ion chromatograms are herein referred to as vacant chromatograms. Next, noise characteristics (e.g., as represented by one or more power density spectra) of the LC-MS data set are determined based on an analysis of noise in the vacant chromatograms, and at least one transfer function is determined based on the noise characteristics. Noise is then reduced in the LC-MS data set by performing matched filtration of the first chromatograms with the transfer function to generate one or more second extracted ion chromatograms, and by generating a noise-reduced LC-MS data set based on the second extracted ion chromatograms. Like the original LC-MS data set, the noise-reduced LC-MS data set is represented by an LC-MS data array having a chromatographic time dimension and a mass spectral dimension. The noise-reduced LC-MS data array is then analyzed in the chromatographic time dimension and the mass spectral dimension to detect one or more peaks within the corresponding data set. It is important to note that noise reduction performed in the chromatographic time domain does not distort the shapes of MS peaks. On the contrary, chemical noise is removed and the MS peaks are made more symmetrical regardless of the S/N value, thus improving the accuracy of peak centroids definition.

Specifically, the noise-reduced LC-MS data array is analyzed in the chromatographic time dimension to detect peak candidates across the range of mass-to-charge (m/z) values in the mass spectral dimension, and a respective peak score value is calculated for each detected peak candidate. For example, the respective peak score values may be calculated based on the shape, width, and/or intensity of the detected peak candidate(s). Next, the noise-reduced LC-MS data array is analyzed in the mass spectral dimension to detect one or more peaks within the data set by comparing the respective peak score values for the peak candidates.

By generating a multi-dimensional data set having respective dimensions corresponding to compound separation and compound characteristic properties, reducing noise in the multi-dimensional data set, and detecting peaks by analyzing the data set in each of the respective dimensions of the data, peaks (i.e., compounds) can be detected, identified, and quantitated with increased reliability in the presence of chemical and/or random noise and with substantially no distortion in the mass spectral domain.

Other features, functions, and aspects of the invention will be evident from the Detailed Description of the Invention that follows.

BRIEF DESCRIPTION OF THE SEVERAL VIEWS OF THE DRAWINGS

The invention will be more fully understood with reference to the following Detailed Description of the Invention in conjunction with the drawings of which:

FIGS. 4a-4c are diagrams illustrating spectra from LC-MALDI-MS chemical noise-reduced by the method of FIG. 2;

FIGS. 10a-10d are diagrams illustrating peak picking by the method of FIG. 2 for the digest of an ICAT labeled yeast sample;

DETAILED DESCRIPTION OF THE INVENTION

U.S. Provisional Patent Application No. 60/372,155 filed Apr. 12, 2002 entitled PEAK PICKING ALGORITHM FOR LC-MS, and U.S. Provisional Patent Application No. 60/440,950 filed Jan. 17, 2003 entitled MATCHED FILTRATION WITH EXPERIMENTAL NOISE DETERMINATION FOR DENOISING, PEAK PICKING AND QUANTITATION IN LC-MS are incorporated herein by reference.

An improved system and method of analyzing samples is disclosed that provides highly reliable peak (i.e., compound) detection and identification in the presence of chemical and/or random noise. The sample analysis system and method reduces noise in a multi-dimensional data set having respective dimensions corresponding to compound separation information and compound characteristic information, and detects peaks in the noise-reduced data set by analyzing the data in each of its respective dimensions.

Figure 1:
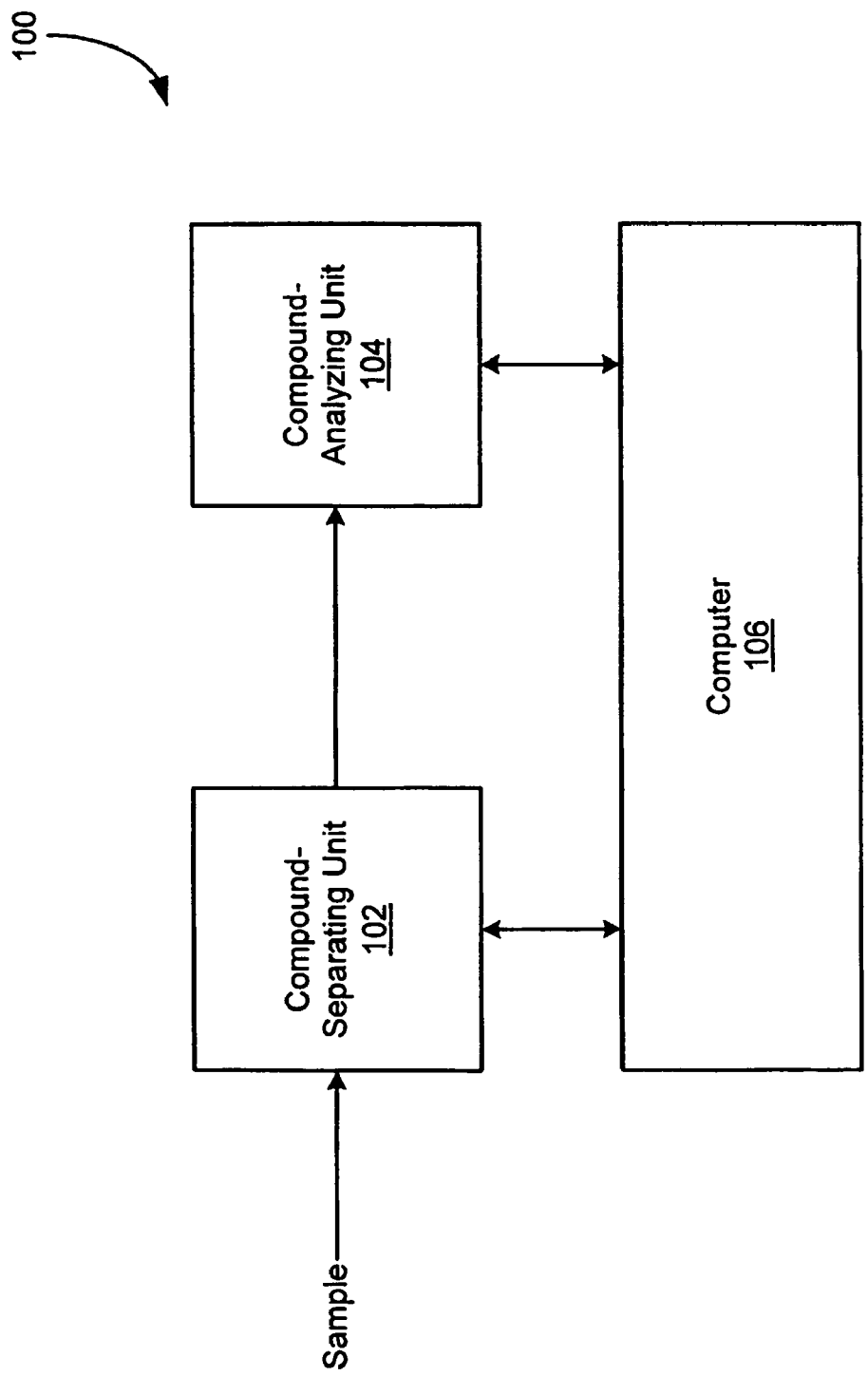
FIG. 1 is a block diagram of a sample analysis system operative according to the present invention.

FIG. 1 depicts an illustrative embodiment of a sample analysis system 100, operative in accordance with the present invention. For example, the sample analysis system 100 may be employed in the field of analytical chemistry for detecting, identifying, and quantitating one or more (typically several hundred) constituent compounds in a sample mixture. In the illustrated embodiment, the sample analysis system 100 includes a compound-separating unit 102, a compound-analyzing unit 104, and a computer 106. The compound-separating unit 102 is configured to separate the constituent compounds in the sample mixture, and the compound-analyzing unit 104 is configured to analyze the separated compounds and to generate data characteristic thereof. Further, the computer 106 is operative to acquire the data generated by the compound-separating unit 102 and the compound-analyzing unit 104, and to analyze the acquired data for identifying and quantitating the constituent compounds. Specifically, the computer 106 generates a multi-dimensional data set incorporating the acquired data, executes an algorithm for reducing noise (e.g., chemical and/or random noise) in the data set and for detecting peaks (i.e., compounds) in the noise-reduced data, and identifies/quantitates the detected compounds.

For example, the compound-separating unit 102 may be operative to perform a liquid chromatographic separation technique, an electro-chromatographic separation technique, an electrophoretic separation technique, or any other suitable separation technique. Further, the compound-analyzing unit 104 may be operative to perform a Mass Spectral (MS) analytic technique, a Nuclear Magnetic Resonance (NMR) analytic technique, a photodiode array detector technique, or any other suitable analytic technique. In addition, for MS, the compound-separating unit 102 may be operative to perform any suitable interface technique to the sample analysis method such as LC-MALDI, LC-ESI, CE-MALDI, CE-ESI, CEC-MALDI, or CEC-ESI. Moreover, the computer 106 may comprise a general-purpose or dedicated computer including at least one memory (not shown) such as ROM and/or RAM for storing operating systems and application software modules, and at least one processor (not shown) for executing one or more sample analysis applications.

For purposes of illustration, the compound-separating unit 102 is configured to perform a Liquid Chromatography (LC) separation technique, and the compound-analyzing unit 104 is configured to perform a Mass Spectrometry (MS) analytic technique. Further, the computer 106 is operative to acquire MS data from the compound-analyzing unit 104 for consecutive time points of chromatography, and to generate a multi-dimensional LC-MS data set. In the illustrative embodiment, the LC-MS data set is represented by an LC-MS data array having a chromatographic time dimension and an MS dimension.

Figure 2:
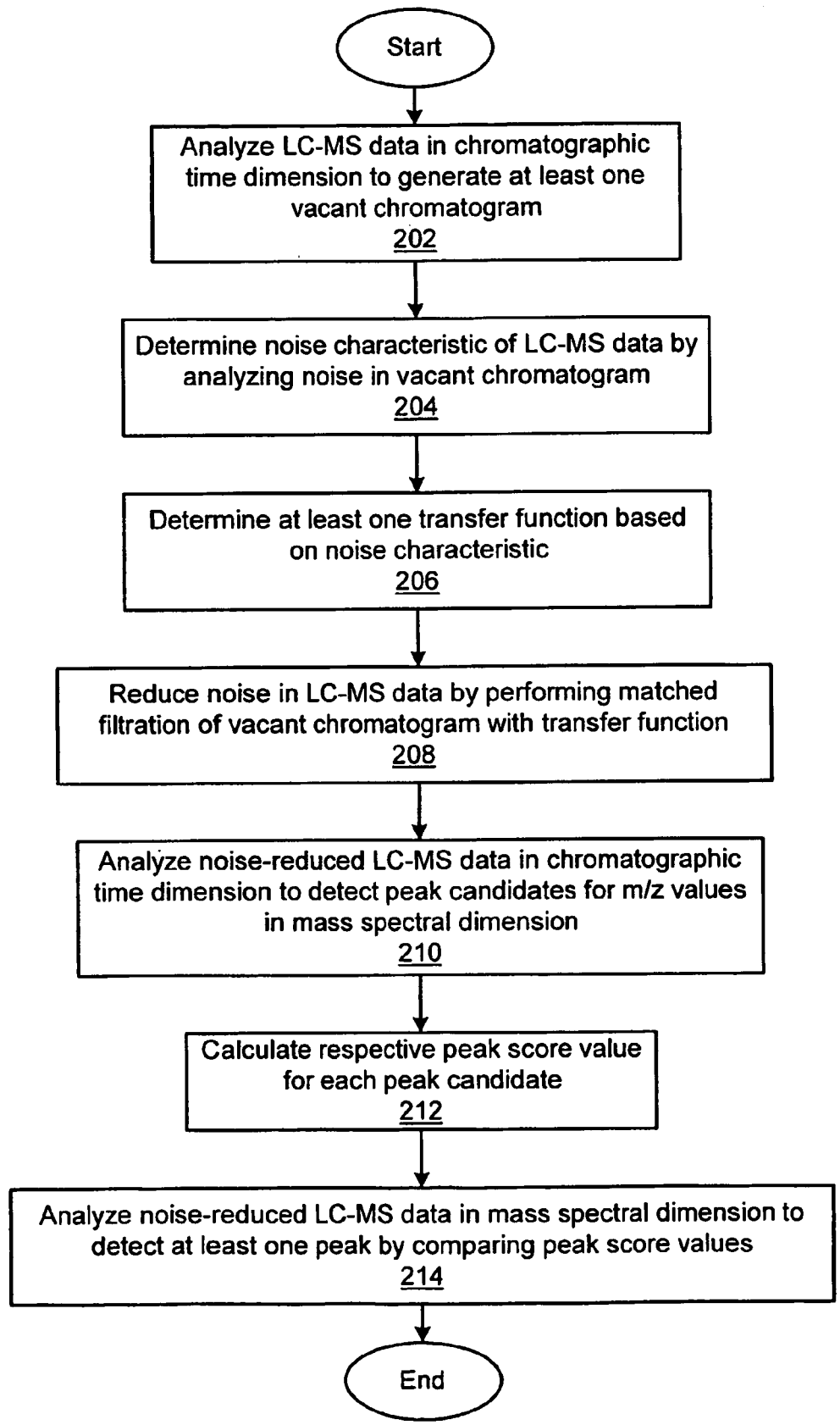
FIG. 2 is a flow diagram of a method of characterizing constituent compounds in a sample mixture using the sample analysis system of FIG. 1.

A method of analyzing an LC-MS data array to characterize constituent compounds in a sample mixture using the sample analysis system disclosed herein is illustrated by reference to FIG. 2. It is noted that the disclosed method has three main parts—(1) the determination of noise characteristics, (2) matched filtration with transfer functions based on the determined noise characteristics, and (3) peak detection ("peak picking") based on the examination and scoring of a plurality of pre-selected peak candidates.

As depicted in step 202, the LC-MS data array is analyzed in the chromatographic time dimension to generate one or more chromatograms having one or more regions in which there are no chromatographic peaks. Chromatographic peaks are defined by the expected shape and peak width depending on the experimental conditions of the separation step. The chromatographic peak-free regions of the original chromatograms are herein referred to as vacant chromatograms. Next, a noise characteristic of the LC-MS data set is determined, as depicted in step 204, based on an analysis of noise in the vacant chromatograms. Such characterization of noise is performed in the chromatographic time domain, in which one or more vacant extracted ion chromatograms including no chromatographic peaks are determined. In the preferred embodiment of the invention, a power density spectrum of the vacant extracted ion chromatograms is calculated and averaged for a predetermined number of extracted ion chromatograms, e.g., about 500.

Next, at least one transfer or correlation function is determined, as depicted in step 206, based on the noise characteristic determined in step 204. In the preferred embodiment of the invention, the transfer function H(f) for matched filtration is determined according to the equation $$H(f) = S^*(f)/P_{NN}(f), \quad (1)$$

in which $S^*(f)$ is the complex conjugate of the Fourier transform of the function presenting the expected shape of the chromatographic peak, and $P_{NN}(f)$ is the power density spectrum of the vacant extracted chromatogram. It is noted that the power density spectrum may be expressed as $$P_{NN}(f) = \int R_{NN}(t) \exp(-j2\pi ft) dt, \quad (2)$$

in which "$R_{NN}$" is the auto-correlation function of the vacant chromatogram. The noise characteristics are mass-to-charge (m/z) dependent (for both LC-MALDI-MS and LC-ESI-MS). The transfer functions are therefore separately determined for a predetermined number of m/z regions, e.g., about 200. For example, the expected shape of the chromatographic peak may be Gaussian, Poisson, or any other suitable shape. Further, it should be appreciated that any other suitable transfer function may alternatively be employed.

Next, noise is reduced, as depicted in step 208, in the LC-MS data set by performing matched filtration of the vacant chromatograms with the determined transfer function(s), thereby generating a noise-reduced LC-MS data array. Specifically, matched filtration of the extracted ion chromatograms for each m/z value (e.g., about 130,000 chromatograms) is performed with the experimentally determined transfer functions. The new data array is constructed by substituting the original extracted ion chromatograms with extracted ion chromatograms noise-reduced by matched filtration. As a result, chemical and random noise are substantially reduced in both the chromatographic time and m/z domains without distorting the MS peaks.

The noise-reduced data array is then analyzed in both the chromatographic time and mass spectral dimensions to allow highly reliable peak picking, even for peaks with low Signal-to-Noise ratio (S/N), e.g., about 3. Specifically, the noise-reduced LC-MS data array is analyzed, as depicted in step 210, in the chromatographic time dimension to detect peak candidates for a plurality of m/z values in the mass spectral dimension, and a respective peak score value is calculated, as depicted in step 212, for each detected peak candidate. Finally, the noise-reduced LC-MS data array is analyzed, as depicted in step 214, for peak picking in the mass spectral dimension by comparing the peak score values for the detected peak candidates.

In this illustrative embodiment, peak picking is performed based on a comparison of scores generated for each of the m/z values with a predetermined threshold $T_p$. A final score $Sc_f$ combining the results of the evaluation of peak candidates in the chromatographic time and m/z domains is calculated as $$Sc_f = Sc \cdot K_v \cdot K_I, \quad (3)$$

in which "Sc" is an initial score determined by examining the peak in the chromatographic time domain, and "$K_v$" and "$K_I$" are determined by examining the MS peak shape and ratios of peak intensities in an isotopic cluster. It should be appreciated that any other suitable peak score calculation technique may alternatively be employed. In the preferred embodiment, only peak candidates with final score values exceeding the threshold $T_p$ are included in a list of peak candidates.

The initial score Sc is calculated as the ratio of the maximum and mean values of the matched-filtered extracted ion chromatograms, and therefore characterizes the S/N for the largest peak in a given chromatogram, for example, $$Sc \approx (S/N) \cdot G, \quad (4)$$

in which "S/N" is the Signal-to-Noise ratio for the largest peak in the chromatogram, and "G" is the gain due to the matched filtration. A high value of Sc indicates the presence of a chromatographic peak, and $Sc \leq 2$ indicates that the maximum and mean values are similar and therefore no chromatographic peaks are present.

To enable the scoring and selection of more than one peak in each extracted ion chromatogram, the largest chromatographic peak is eliminated after being detected. Matched filtration is then repeated, and the next largest peak in the extracted ion chromatogram is detected and scored. In the preferred embodiment, this process is repeated M times, in which M is equal to the expected maximum number of chromatographic peaks in the extracted ion chromatogram. The expected maximum number of chromatographic peaks is generally dependent upon the complexity of the sample mixture and the resolution of the mass spectrometry instrument (e.g., the higher the resolution, the lower the M value). For example, M may be equal to 5, but may be doubled if necessary for more complex sample mixtures without significantly increasing the computation time.

By noise-reducing and peak-scoring in the chromatographic time domain, a number of peak candidates (typically several thousand) are pre-selected for the peak candidate list. As a result, the number of data points that need to be further analyzed is significantly reduced relative to the initial several hundred million points (e.g., about 130,000×3,000 for a typical data set).

For each peak candidate, the m/z value, the spectrum number (i.e., the chromatographic time point where the peak apex is observed), and the intensity are known. The intensity of the peak candidate is then compared to intensities of candidates corresponding to neighboring m/z values. For example, five neighbors at lower and higher m/z values relative to the peak candidate may be examined. The coefficient $K_v$ is then generated, and the highest value of $K_v$ is assigned to the peak candidate in the event (1) the intensities of all of its five neighbors at the lower m/z values monotonically increase, and (2) the intensities of all of its neighbors at the higher m/z values monotonically decrease. For each deviation from the above-described behavior, the value of $K_v$ is decreased by a factor of $d_v$. As a result, the highest values of $K_v$ are assigned to the peak candidates representing apexes of MS peaks having smooth shapes.

Next, the ratios of the peak heights of isotopes in the isotopic clusters are compared to the theoretically predicted values. The closer the peak height ratios are to the theoretically predicted values, the higher the coefficient $K_I$. It is noted that reducing the noise in the data set aids in the determination of accurate ratios of the isotope peak heights. The maximum value $K_{Imax}$ is assigned in the event all of the peaks in the isotopic cluster have peak height ratios that agree with the theoretically predicted values. For each isotope with peak height ratios that are different from the theoretically predicted values, the $K_I$ value is decreased by the factor $d_v$.

It should be noted that the optimal values of $K_{Vmax}$ and $K_{Imax}$ and their respective factors of decrease $d_v$ and $d_I$, and the optimal value of the threshold $T_p$ for final peak selection depend upon the type of mass spectrometry instrument used (i.e., both the type of ion source and the type of mass analyzer). For example, the mass resolution affects not only the widths of the MS peaks, but also the observed ratios of the isotopes in the isotopic clusters. For a lower resolution instrument, experimentally observed signals from the isotopic clusters are either de-convoluted before comparison with theoretically predicted ones, or the examination of the shape of the isotopic cluster is made more tolerant (i.e., smaller $d_I$) to account for possible deviations from the theoretical predictions.

Next, the mono-isotopic peaks are selected from the isotopic clusters (herein referred to as de-isotoping). For the case of LC-MALDI-MS, peaks corresponding to sodium and potassium adducts are determined and eliminated from the peak candidate list (herein referred to as de-adducting). Optionally, additional removal of matrix clusters/peaks may be performed based on the prediction of the m/z regions prohibited for peptides.

For complicated cases like overlapping isotopic MS clusters or overlapping isotopically labeled pairs, in which it is important to make sure that two or more components of the mixture are co-eluting, chromatographic profiles of these components are automatically selected and compared by calculating the cross-correlation function of the extracted ion chromatograms corresponding to these components. A high value of the ratio of the maximum of the cross-correlation function to its mean value is indicative of the similarity of the chromatographic elution profiles of the examined components, thus enabling natural isotopes and/or isotopically-labeled components having the same elution profile as the mono-isotopic peak to be distinguished from different components having similar elution time but different chromatographic elution profile.

The sample analysis method disclosed herein allows low intensity peak picking and the determination of peak centroids with increased mass accuracy. The sample analysis method also provides increased S/N by suppressing chemical noise, reducing peaks originating from matrix (MALDI) or mobile phase (ESI), and suppressing low frequency fluctuations of the m/z base line.

It is understood that some peaks that are well resolved in the MS mode (LC/MS) may be overlapping in the tandem MS (LC/MS/MS) mode. Such peaks are overlapping in the chromatographic time domain, and are typically within a precursor ion selection window of MS/MS instrument. MS/MS spectra from such overlapping peaks can lead to an increase in false positive identifications. A method of quantitating the level of peak overlapping in the MS/MS mode and for reducing the effect of this overlapping by redistributing MS/MS candidates (precursor ions) between MS/MS wells is described below.

According to the above-described sample analysis method, selection of the candidates for MS/MS analysis based on quantitation of the level of overlapping of peak candidates (i.e., ovlp) is provided as $$ovlp = \sum_{i=1}^{M} C_i \cdot \exp(-\Delta t_i^2 / 2\sigma_i^2) / C_0, \quad (5)$$

in which M is the number of peaks within an MS/MS window having an intensity greater than a predetermined portion (e.g., 0.05) of the main peak, Ci is the intensity of the overlapping peaks, $\Delta t_i^2$ is the distance between the main peak and the overlapping peak in the chromatographic time domain, and $\sigma_i$ is the chromatographic peak variance. The overlapping of peaks is a result of the relatively broad MS/MS window (e.g., 10 Daltons (Da) in case of a TOF-TOF MS instrument) and the complexity of the analyzed mixture. It occurs for about 20% of peaks in the case of complex mixtures like tryptic digests in Proteomics. To reduce the effect of the overlapping peaks, the overlapping peaks are determined and their level of overlapping is quantified. Next, different precursors are selected, if possible. The MS/MS wells are then re-distributed to reduce the level of peak overlapping, and peaks with low overlapping are selected. Next, to increase the number of peaks suitable for identification, the MS/MS wells are selected with not more than two overlapping peaks of commensurate intensity in one well. The precursor ion m/z values for the two peaks are then selected, and both are submitted for data base search. Regions on the MALDI plate with no MS/MS peak candidates are also selected, and additional MS/MS candidates (having lower thresholds of intensity and S/N) are selected, and their level of overlapping is determined. By decreasing the number of overlapping peaks, it is possible to decrease the likelihood of false positive peak identifications.

Benefits of the above-described sample analysis system and method are illustrated by the following examples. Specifically, Example 1 addresses the problem of reducing noise in LC-MALDI-MS data sets, Example 2 addresses the affect such noise reduction has on the mass accuracy, Example 3 addresses the problem of reducing noise in LC-ESI-MS data sets, and Example 4 addresses peak picking for LC-MALDI-MS in complex sample mixtures. Examples 1-4 show that the method disclosed herein significantly decreases both chemical and random noise, thereby increasing S/N and enabling the detection of low intensity peaks. It is further shown that the noise reduction technique does not distort MS peak shape, resulting in high mass accuracy. Moreover, it is demonstrated that the above-described method may be effectively employed to reduce noise in data from LC-ESI-MS. An example of the application of the disclosed noise reduction and peak picking technique to the LC-MALDI-MS analysis of digests of complex protein mixtures is also described below.

EXAMPLE 1

Noise Reduction in LC-MALDI-MS Data Sets

Figure 3A:
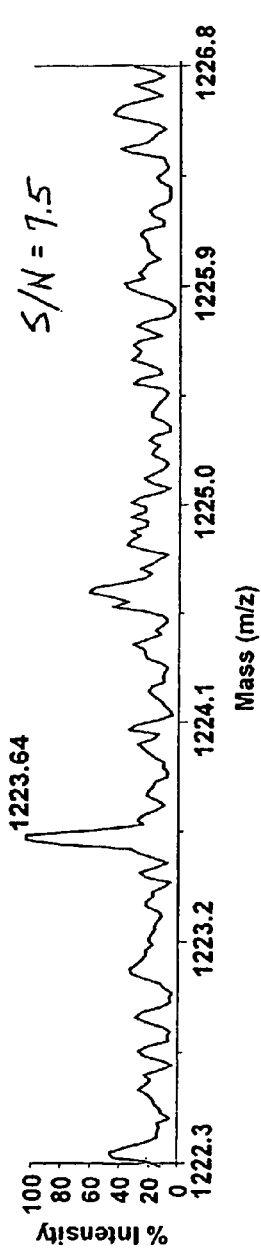
FIGS. 3a-3b are diagrams illustrating spectra from LC-MALDI-MS noise-reduced by conventional noise-reducing techniques.
Figure 3B:
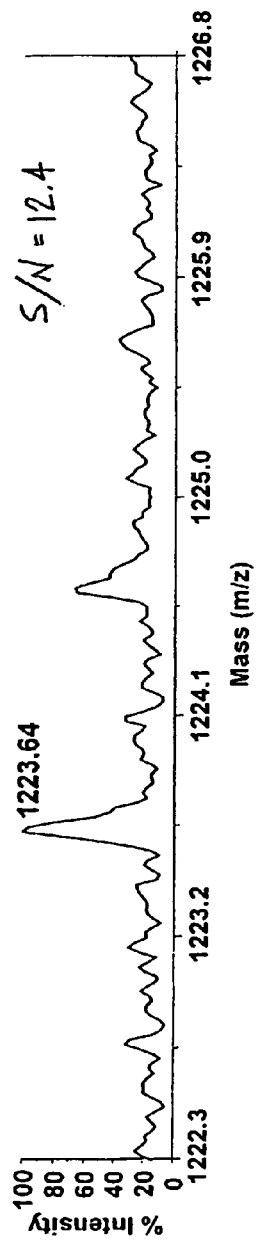
Figure 3C:
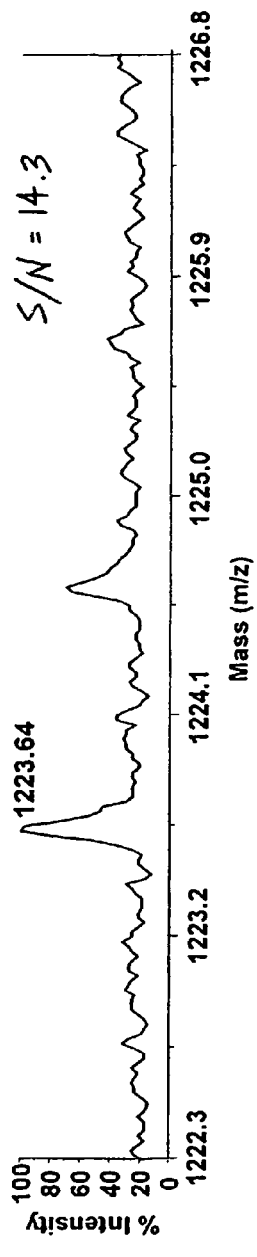
FIGS. 3c-3d are diagrams illustrating spectra from LC-MALDI-MS noise-reduced by the method of FIG. 2.
Figure 3D:
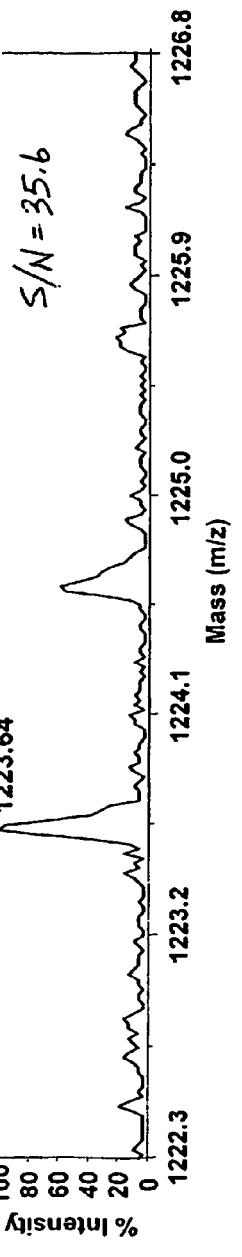

It should be appreciated that the suppression of chemical and random noise is important for the generation of accurate peak lists. FIGS. 3a-3d depict noise reduction of a typical mass spectrum from an LC-MALDI-MS data set produced by the analysis of a mixture of 10 standard peptides (see SAMPLES below, Sample 1). Specifically, FIG. 3a depicts a representative original spectrum corresponding to one second of chromatography resulting from averaging a signal from 150 laser shots; FIG. 3b depicts the result of moving-averaging of 10 consecutive spectra from the original data set (corresponding to 10 seconds of chromatography and 1500 laser shots); FIG. 3c depicts the result of noise reduction by cross-correlation of the Gaussian (i.e., matched filtration assuming random noise); and, FIG. 3d depicts the spectrum noise-reduced by matched filtration according to the method of FIG. 2 (i.e., using experimentally-determined noise characteristics). It can be seen by comparing the spectrum of FIG. 3d to the original spectrum of FIG. 3a that matched filtration based on the experimental determination of the noise characteristics improves noise reduction (S/N=35.6 for the spectrum of FIG. 3d, S/N=7.5 for the spectrum of FIG. 3a). Further, by comparing the spectrum of FIG. 3d to the spectra of FIGS. 3b-3c, it is shown that the above-described method suppresses the background noise significantly more than the averaging of 10 spectra (S/N=12.4) and cross-correlation with the Gaussian (S/N=14.3).

FIGS. 4a-4c depict noise reduction for an LC-MALDI-MS data set in a complex sample mixture, i.e., a Strong Cation Exchange (SCX) fraction of tryptic digest of yeast sample (see SAMPLES below, Sample 3). By comparing the noise-reduced spectrum of FIG. 4c (S/N=46.2) to the original spectrum of FIG. 4a (S/N=5.5), it can be seen that the S/N is improved by a factor of 8. Further, by comparing the spectrum of FIG. 4c to the 10 spectra-averaged spectrum of FIG. 4b (S/N=18.6), it is seen that the S/N is improved by a factor of 2.5. It is noted that in the averaged spectrum (see FIG. 4b), the 1 Da periodicity of the chemical noise can be clearly seen. Matched filtration according to the above-described method suppresses chemical noise to a significant extent, and therefore not only improves the shapes of the MS peaks and consequently the accuracy of their centroid determination, but also reduces the likelihood of false positives.

The method disclosed herein suppresses undesirable peaks originating from standards added to the matrix, as depicted in FIGS. 5a-5e. The sample analyzed by LC-MALDI-MS is a mixture of 10 standard peptides (see SAMPLES below, Sample 1), and five standards are added to the matrix for calibration purposes. The spectrum of FIG. 5a results from the averaging of 10 consecutive spectra, and the spectrum of FIG. 5b results from application of the above-described method. It can be seen that the peak corresponding to Tyr-bradykinin (m/z=1223.64) is much more intense in the case of matched filtration (see FIG. 5b) than for 10 spectra averaging (see FIG. 5a). It can also be seen that there are peaks (e.g., m/z=1233.61, m/z=1252.67) in the averaged spectrum (see FIG. 5a) that are not present in the spectrum resulting from matched filtration (see FIG. 5b).

Figure 5A:
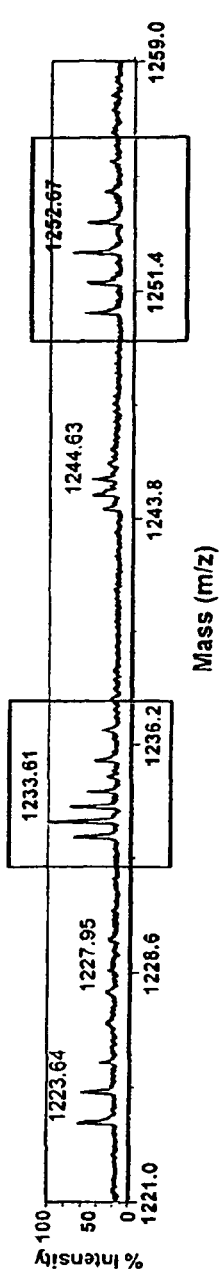
FIGS. 5a-5e are diagrams illustrating spectra from LC-MALDI-MS having matrix-related peaks removed by the method of FIG. 2.
Figure 5B:
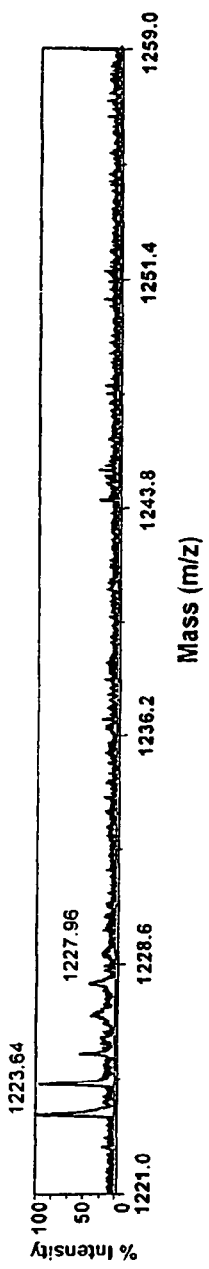
Figure 5C:
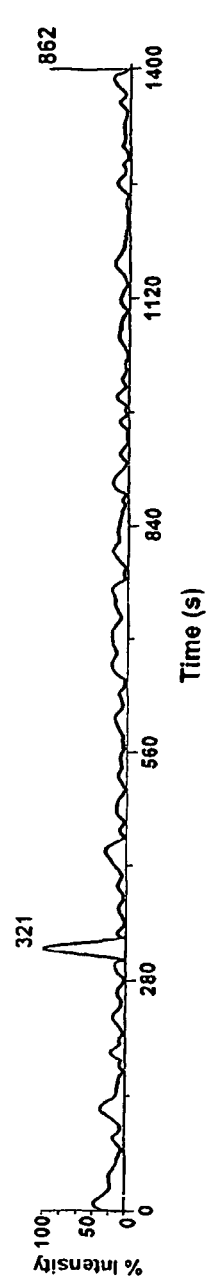
Figure 5D:
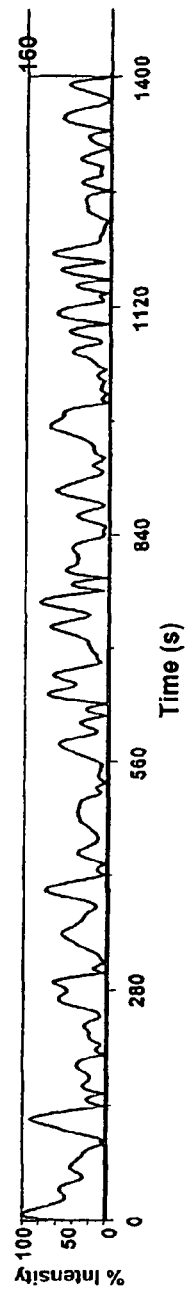
Figure 5E:

Analysis of the corresponding matched-filtered Extracted Ion Chromatograms (EIC) at m/z=1223.64 (see FIG. 5c), at m/z=1233.61 (see FIG. 5d), and at m/z=1252.67 (see FIG. 5e) shows that a chromatographic peak is present for m/z=1223.64. FIGS. 5d-5e merely indicate oscillating behavior with maxima roughly 5-8 times smaller than that of FIG. 5c. It is evident that the ions m/z=1233.61 and m/z=1252.67 are present in essentially all of the spectra and must therefore arise from the matrix solution. It is further noted from FIG. 5a that isotopes in the m/z=1233.61 cluster are separated not by 1 Da, but by 0.5 Da. It is therefore a doubly-charged ion, and its source is the internal standard peptide ACTH 18-39 with molecular weight 2465.20 Da. The cluster at m/z=1252.67 represents singly-charged ions with 1 Da separation between isotopes—it could therefore be a cluster of matrix ions or the result of the adduction of matrix ions with the standards. It should be appreciated that these ions are not present in the analyzed sample.

Accordingly, the disclosed method can effectively eliminate matrix solution peaks. If these matrix peaks are not filtered out, then they could cause false identifications. It is possible to remove such false peaks by examining EICs for each and every picked peak, and determining whether or not it represents a real chromatographic peak. However, via the above-described method, these matrix peaks are eliminated simultaneously with noise reduction.

EXAMPLE 2

Mass Accuracy in LC-MALDI-MS Noise-Reduced Data Sets

FIGS. 6a-6d illustrate the non-distorting character of the disclosed method, even for peaks with low S/N. In this illustrative example, the tryptic digest of a model mixture of 7 proteins (see SAMPLES below, Sample 2) is analyzed by LC-MALDI-MS. Further, the peak list is generated and used for selecting precursor ions for MS/MS analysis, and the results of MS/MS analysis are submitted to the MASCOT™ search engine, which is provided by Matrix Science Ltd., London, England. Thirty-nine peptides are identified. The sample is then diluted 5 times, and 5 standards are added to the matrix solution to provide mass calibration. Due to the combined effect of the dilution and ion suppression caused by the standards, the intensities of the MS peaks are significantly reduced, and only 12 of the 39 peptides identified at the first stage of experiment (high concentration sample) are subsequently detected at the second stage of experiment (diluted sample). For those detected peptides, the S/N varies from 3-14.5.

Figure 6A:
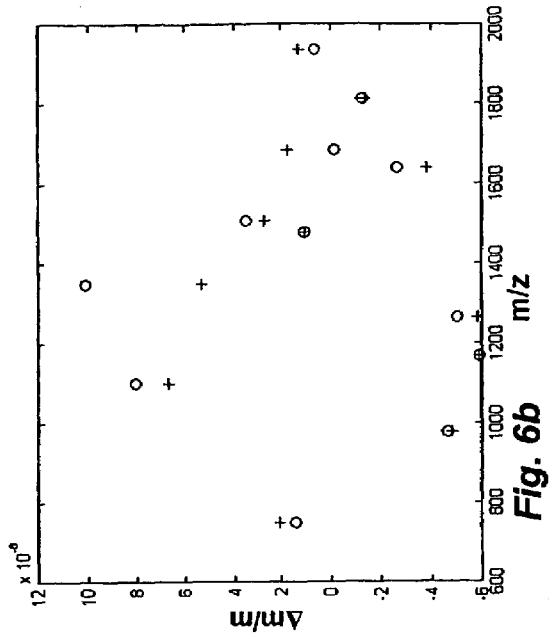
FIGS. 6a-6d are diagrams illustrating the non-distorting character of the method of FIG. 2 for peaks with low signal-to-noise ratio.
Figure 6B:
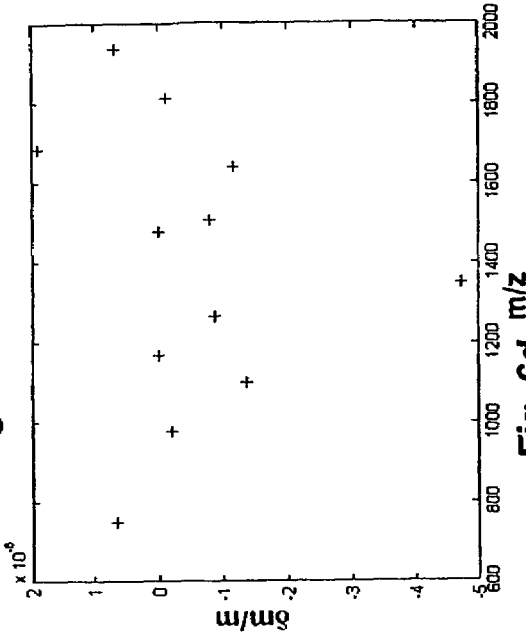

The mass accuracy $\Delta m/m$ is calculated as the difference between the theoretical and experimentally observed m/z values divided by theoretical value. FIG. 6a shows mass accuracy versus S/N, and FIG. 6b mass accuracy versus m/z. Crosses "+" stand for values determined from spectra that are noise-reduced by the above-described method, and circles "o" stand for values resulting from 10 spectra averaging. No clear dependence of mass accuracy on S/N or m/z is observed. For the crosses, the mean value is 3.5 ppm and standard deviation is 4.1 ppm. For the circles, the mean value is 3.7 ppm and standard deviation is 4.7 ppm. Examination of the quality of mass calibration shows that the mass accuracy of calibration is at the same level (standard deviation 3.6 ppm).

Figure 6C:
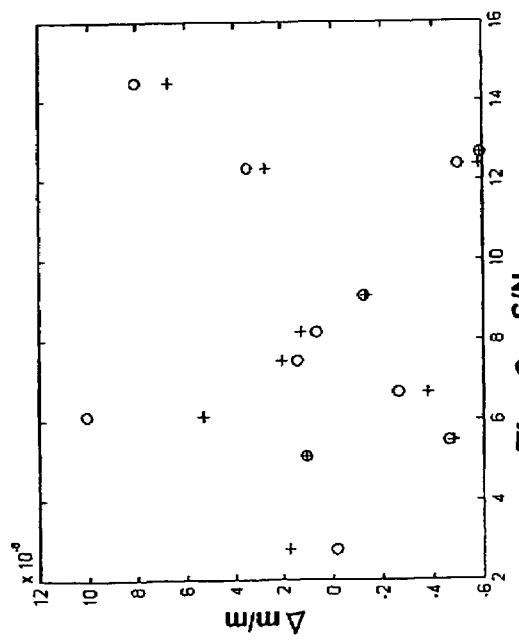
Figure 6D:
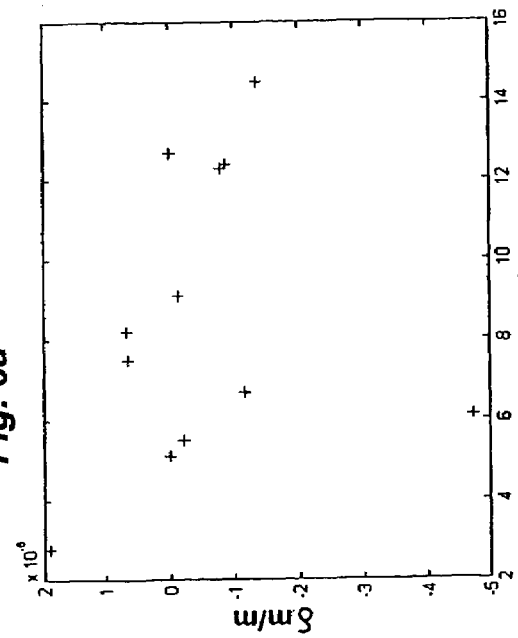

FIGS. 6c-6d depict $\delta m/m$, i.e., the normalized difference between the experimental m/z values of the peptide centroids derived from the data set processed by averaging and matched filtration, respectively. It can be seen that $\delta m/m$ decreases with S/N with no dependence on m/z. The average value of $\delta m/m$ is 1.0 ppm and the standard deviation is 1.5 ppm. The observed mass accuracy for detected peptides is therefore limited not by the chemical noise and its method of reduction, but by the accuracy of the mass calibration. Accordingly, if the mass calibration is improved, the above-described method can provide significantly higher mass accuracy than 10 spectra averaging.

Figures 7A, 7B, 7C:
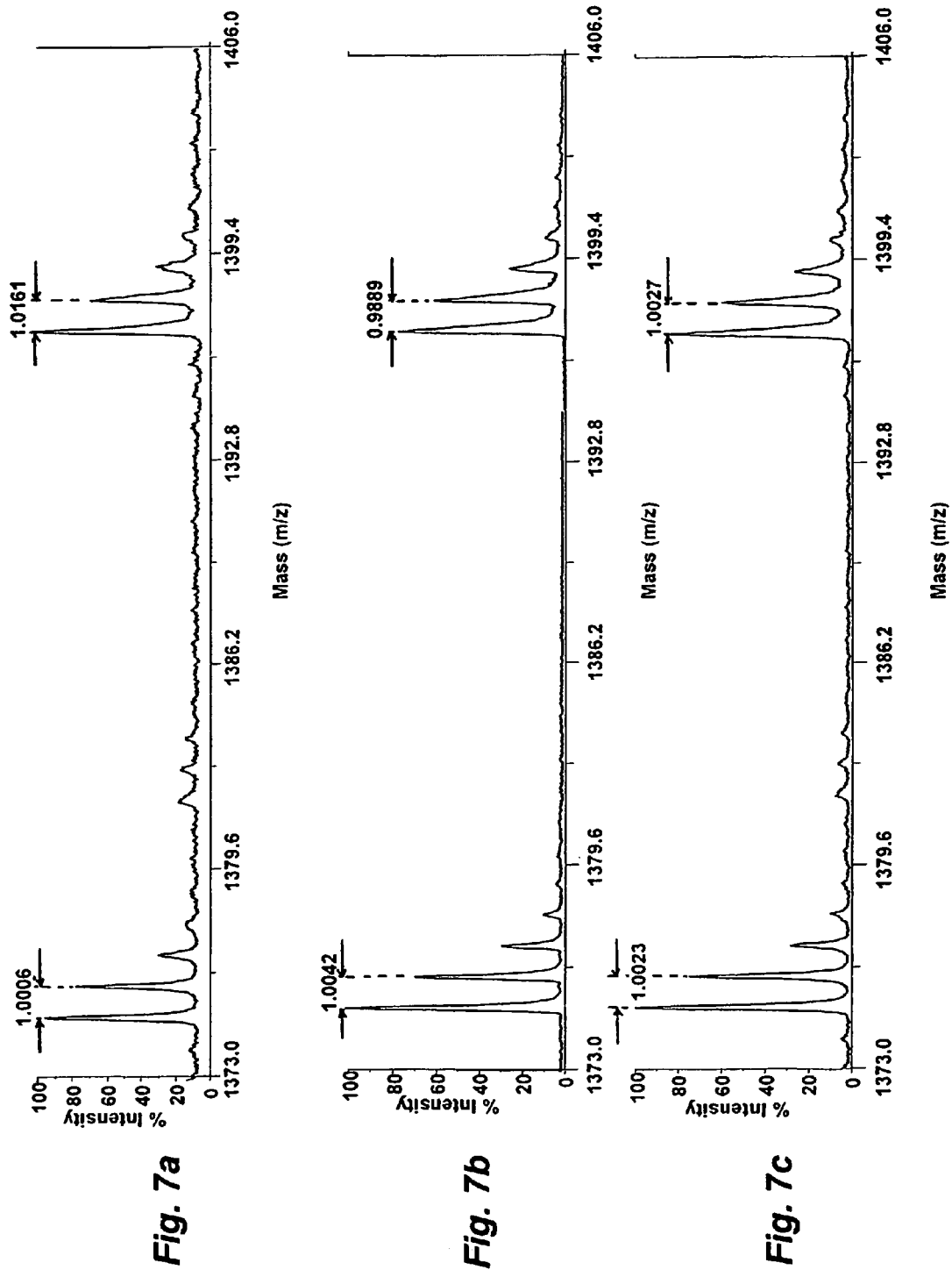
FIGS. 7a-7c are diagrams illustrating spectra from LC-MALDI-MS in which the noise-reducing effect of the method of FIG. 2 on mass accuracy is shown.
Figure 8A:
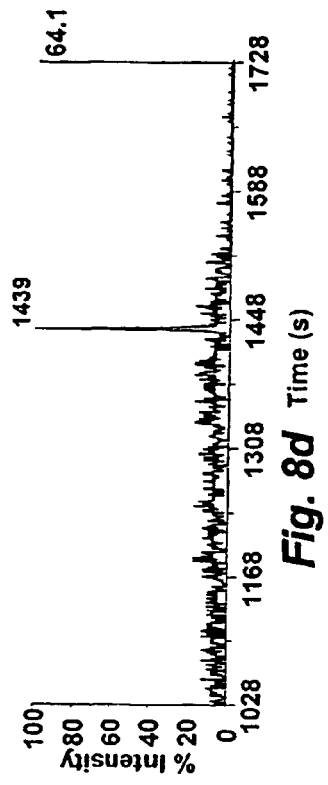
FIGS. 8a-8f are diagrams illustrating noise reduction of data from LC-ESI-MS by the method of FIG. 2.
Figure 8B:
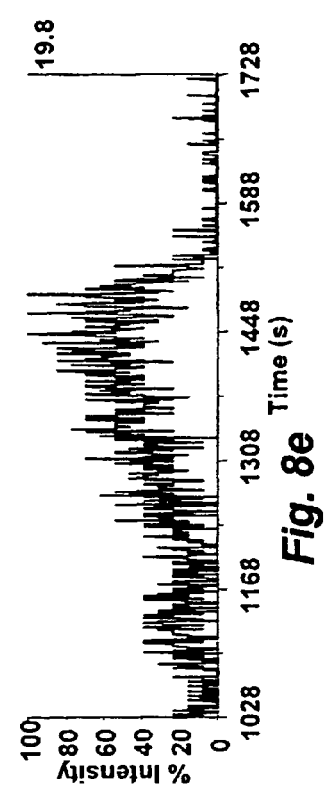
Figure 8C:
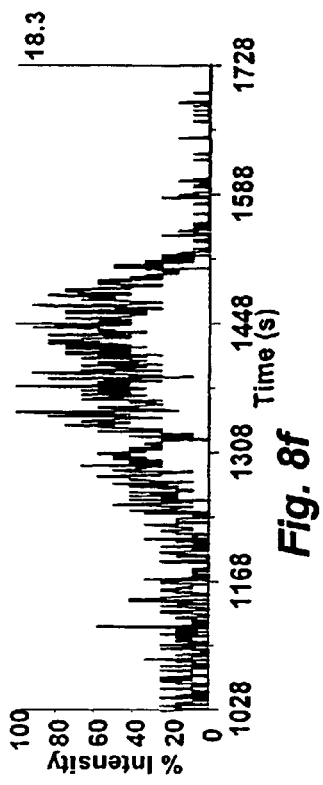
Figure 8D:
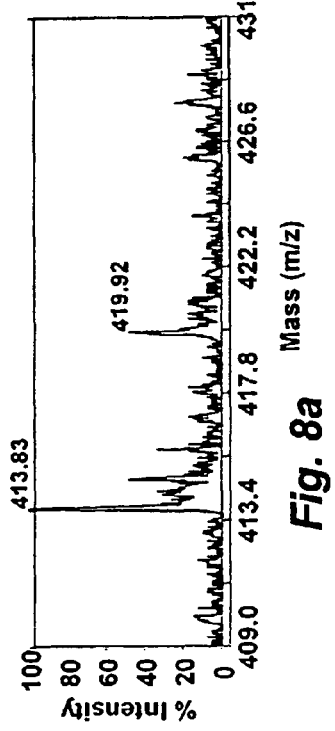
Figure 8E:
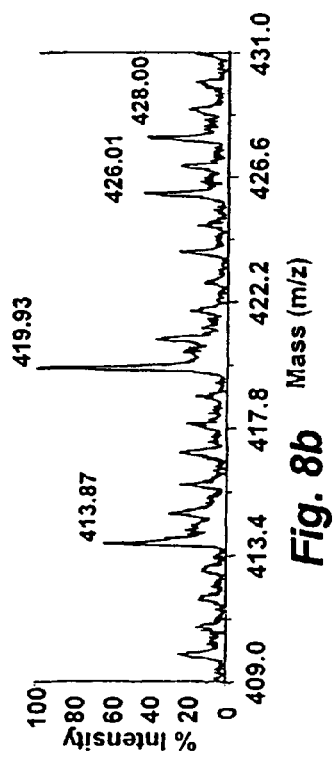
Figure 8F:
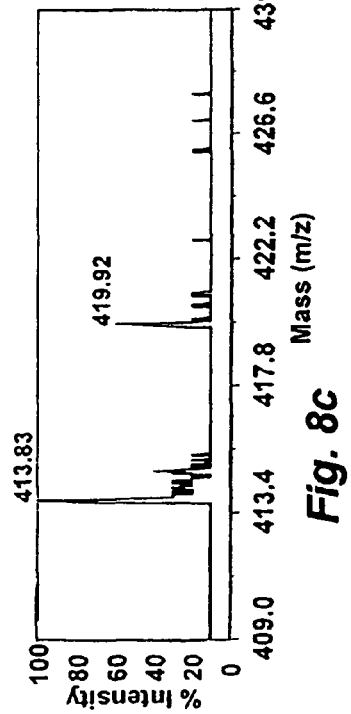

FIGS. 7a-7c show how mass accuracy is influenced by various noise reduction techniques. The data set is produced by LC-MALDI-MS analysis of an intermediate ($8^{th}$ of 23) fraction of SCX of the tryptic digest of yeast lysate (see SAMPLES below, Sample 3). FIG. 7a depicts the spectrum produced by 10 spectra averaging; FIG. 7b depicts the result of second derivative Gaussian filtering; and, FIG. 7c depicts the spectrum due to noise reduction via the above-described method. To exclude the effect of mass calibration on mass accuracy, the distances $\Delta m/z$ between isotopes in the isotopic clusters are examined, instead of examining m/z directly. It is known that the distance between the first two isotopes in an isotopic cluster equals about 1.003. The closeness of the experimentally determined spacing between the peaks in the isotopic clusters to the theoretically predicted value provides a good indication of the quality of noise reduction and the resulting mass accuracy.

For example, matched filtration using the above-described method results in a mass accuracy of 0.4 ppm (calculated based on the spacing between first and second isotopes of the isotopic clusters, see FIG. 7c), while second derivative Gaussian filtering results in a mass accuracy of 5.5 ppm (see FIG. 7b) and 10 spectra averaging leads to a mass accuracy of 5.6 ppm (see FIG. 7a). It can be seen that the shapes of the MS peaks are more symmetrical for the case of matched filtration (see FIG. 7c), indicating an improved reduction of chemical noise. In addition, baseline oscillations are efficiently suppressed in FIGS. 7b-7c, while in FIG. 7a these oscillations are significant. It is therefore shown that the method disclosed herein can improve mass accuracy by reducing chemical noise due to processing in the chromatographic time domain.

EXAMPLE 3

Noise Reduction in LC-ESI-MS Data Sets

FIGS. 8a-8f depict an example of the application of the above-described method to the analysis of LC-ESI-MS data. In the case of 10 spectra averaging (see FIG. 8b), random noise is suppressed, but chemical noise with 1 Da periodicity is higher than in the original spectrum (see FIG. 8a). The noise-reduced spectrum (FIG. 8c) is essentially free of random noise and chemical noise. Peaks at m/z=426.01 and 428.00 are present in both the original spectra (see FIG. 8a) and the 10 averaged spectra (see FIG. 8b), but are absent in the spectrum noise-reduced by the above-described method (see FIG. 8c). As can be seen from the extracted ion chromatograms for these m/z values in FIGS. 8e-8f, the MS peaks are suppressed because they do not correspond to any chromatographic peaks. Rather, they result from the chemical noise due to some impurities of the eluent, and are therefore present in the broad chromatographic time region. The MS peak at m/z=413.83 is present in the noise-reduced spectrum because, as can be seen from extracted ion chromatograms of FIG. 8d, it corresponds to the real chromatographic peak. Accordingly, the capability of the above-described method to distinguish sample components from mobile phase impurities is demonstrated.

Examination of the values of centroids calculated for the original spectrum (see FIG. 8a), the averaged spectrum (see FIG. 8b), and the noise-reduced spectrum (see FIG. 8c) shows that averaging has a tendency to shift centroids to the right in comparison with original values. The centroids for the noise-reduced spectrum are closer to the original ones. Thus, for LC-ESI-MS data, the above-described method demonstrates the same properties as for LC-MALDI-MS data—it suppresses both chemical and random noise, distinguishes sample components from eluent contaminants, and does not compromise the mass accuracy.

EXAMPLE 4

Peak Picking for LC-MALDI-MS of Complex Samples

Figure 9A:
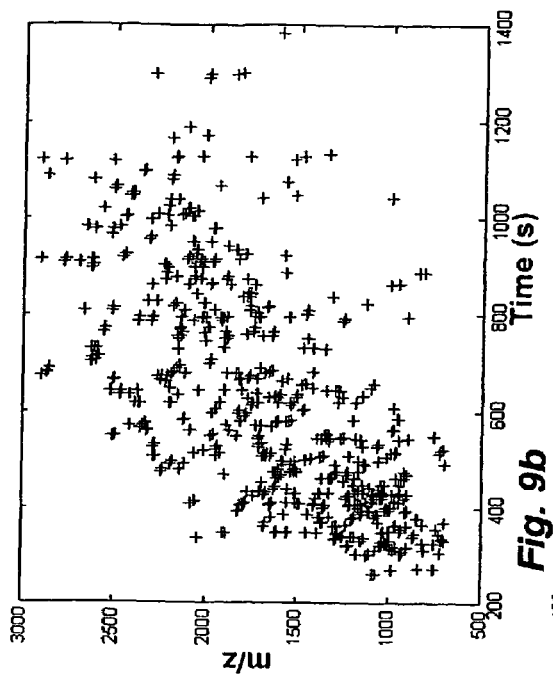
FIGS. 9a-9d are diagrams illustrating peak picking by the method of FIG. 2 for a complex sample mixture analyzed by LC-MALDI-MS.
Figure 9B:
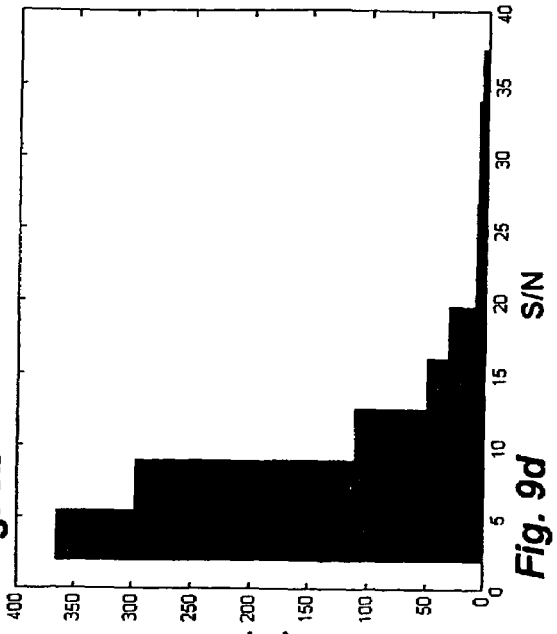
Figure 9C:
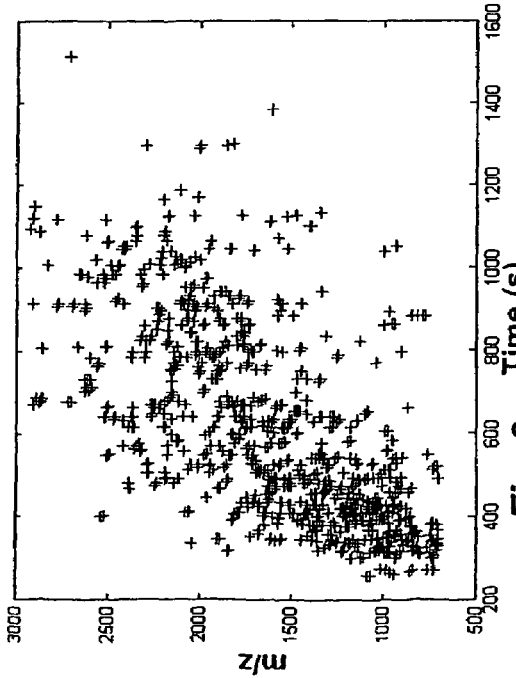
Figure 9D:
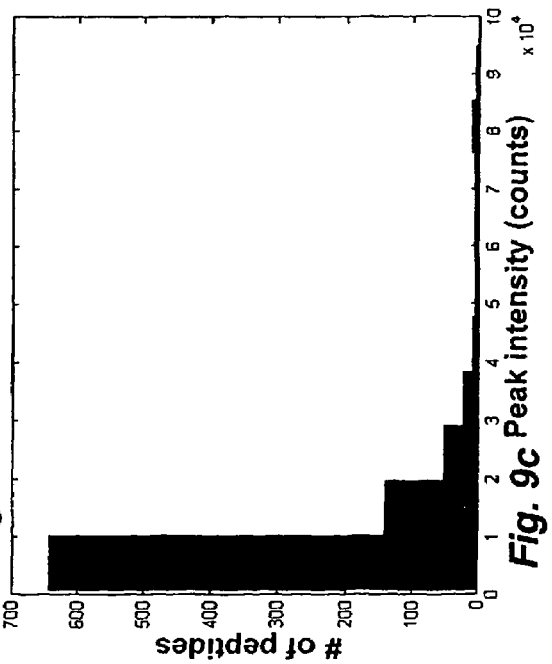

FIGS. 9a-9d and 10a-10d depict the application of the disclosed method to the analysis of LC-MALDI-MS data for complex samples, i.e., fractions of yeast lysate prepared and fractionated. FIGS. 9a-9d show results of an analysis of an intermediate fraction of SCX of yeast lysate (see SAMPLES below, Sample 3). A total of 890 peaks are selected (the distribution of peaks in the chromatographic time and m/z domains is illustrated in FIG. 9a), and among them 601 had intensity higher than 1000 counts and S/N greater than 5 (see FIG. 9b). It can be seen that although the density of the peaks is higher in the region of relatively low masses (m/z<2000), there are still many peaks in the high mass region (about 230 peaks with m/z>2000), and 176 of these 230 peaks have S/N>5. Histograms showing the number of peaks with different intensities and different S/N are shown in FIGS. 9c-9d. About 27% of the total number of peaks have intensity above 10000 counts, and about 39% of initially selected peaks have S/N<5. Accordingly, intensity and S/N of peaks are correlated, but not directly proportional.

FIGS. 10a-10d depict the use of the above-described method for protein expression analysis, and show the results of its application to the analysis of an intermediate fraction of SCX of ICAT labeled yeast proteins digest (see SAMPLES below, Sample 4). Six hundred ICAT pairs are selected and their quantitative analysis is performed by calculation of the volumes of 3-D peaks, corresponding to the LC-MS data noise-reduced by the above-described method. The volume of such peaks is a more robust measure of the amount of the corresponding peptides than either the peak amplitude from a single mass spectrum or the area of chromatographic peak from a single extracted ion chromatogram for a given m/z. Noise reduction by the above-described method aids in determining the values of the peak volumes. Distributions of initially selected peaks, selected ICAT pairs, pairs having S/N>8, and differentially expressed ICAT pairs are shown in FIGS. 10a-10d, respectively. It can be seen that the above-described method significantly decreases the amount of data to be analyzed, and therefore provides a useful tool for high throughput Proteomics.

Figure 11A:
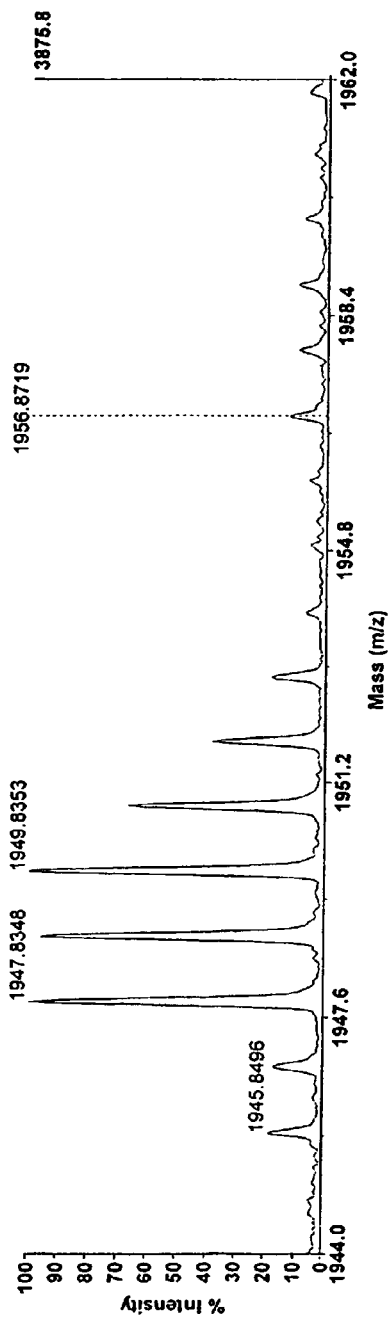
FIGS. 11a-11b are diagrams illustrating the picking of ICAT pairs due to the prior noise reduction of the data by the method of FIG. 2.
Figure 11B:
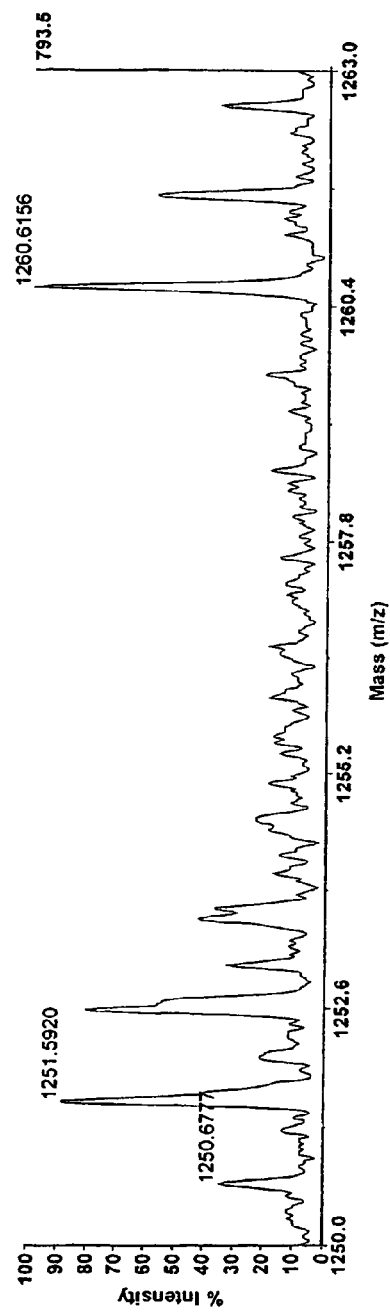

An advantage of the method disclosed herein is its capability of picking low intensity peaks, which is particularly important for analyzing differential expression of proteins, e.g., using the ICAT approach. By picking the low intensity member of the ICAT pair, the above-described method enables the determination of the high intensity one at the distance of 9, 18, or 27 Da as a member of the pair, and performs MS/MS analysis and identification on it. Higher mass accuracy, especially higher accuracy in the determination of the spacing between peaks, results in the capability of specifying smaller mass tolerances for picking of ICAT pairs, and therefore allows a decrease in the likelihood of false positive selection of pairs. Results of the analysis of an ICAT labeled mixture of 5 proteins (see SAMPLES below, sample 5) indicates that by the above-described method, it is possible to select at least 30% additional ICAT pairs using the noise reduction technique. Examples of ICAT pairs (i.e., tryptic digest of ICAT labeled 5 protein mixture) selected by the above-described technique are shown in FIGS. 11a-11b.

Results of the application of the disclosed method to the selection of MS/MS candidates with a reduction of overlapping peaks are tabulated in TABLES I-III, which include analysis results relating to the SCX fraction of yeast lysate digest.

TABLE I

Results of Peak Picking - MS/MS Candidates Selection (LC-MALDI-MS, Yeast Fr 8)

| | |
|---|---|
| Number of peaks after de-isotoping | 3460 |
| Number of peaks after de-adducting | 3113 |
| Number of peaks with intensity above 1000 | 907 |
| Number of peaks with S/N above 5 | 502 |

TABLE II

Number of Peaks with Different Overlapping Level (ovlp)

| | |
|---|---|
| ovlp < 0.1 | 328 |
| 0.1 < ovlp < 1 | 138 |
| ovlp > 1 | 36 |

TABLE III

MS/MS Candidates

| | |
|---|---|
| Selected candidates for MS/MS - ovlp < 0.2 | 375 |
| Wells with two peaks (two precursor ions) | 28 |
| Additional MS/MS candidates from "empty" plate regions" with S/N > 4, ovlp < 0.2 | 52 |
| TOTAL MS/MS CANDIDATES | 455 |

Figure 12A:
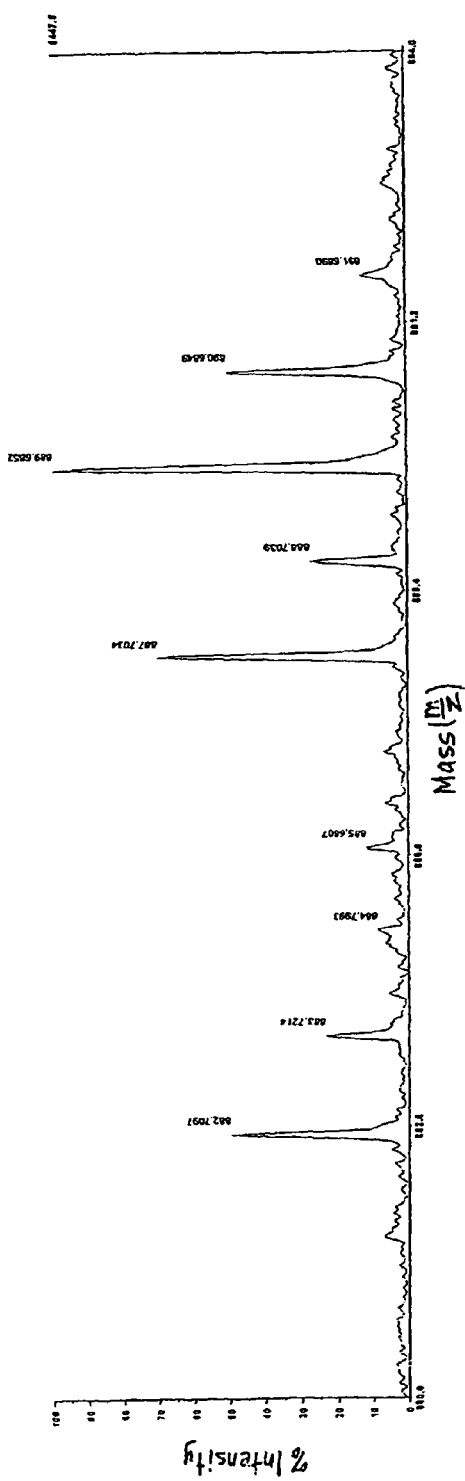
FIGS. 12a-12b are diagrams illustrating peaks discarded due to overlapping according to the present invention.
Figure 12B:
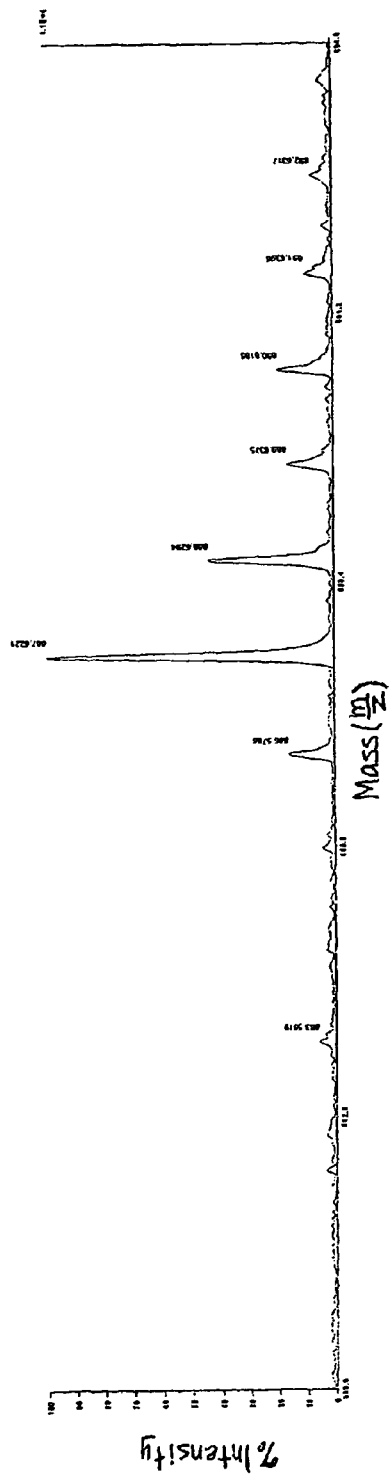

As indicated above, 20% of the initially selected peaks had an overlapping level above 0.2 and were discarded from the list of MS/MS candidates. Further, an additional 52 peaks were selected from the relatively "empty" plate regions. Examples of peaks discarded due to overlapping are shown in FIGS. 12a-12b. It can be seen that these peaks belong to the overlapping isotopic clusters corresponding to co-eluting peptides.

SAMPLES

Sample 1—Mixture of 10 Model Peptides

All peptides were obtained from the Sigma Chemical Co., St. Louis, Mo., U.S.A. (see TABLE IV).

TABLE IV

Model and Standard Peptides

| Peptide | m/z |
|---|---|
| Angiotensin II Human, fragment 1-7 | Sample 899.4739 |
| Angiotensin II HUMAN | Sample 931.5149 |
| Sar1-Angiotensin II | Sample 1002.5525 |
| Tyr8-Bradykinin | Sample 1223.6326 |
| Substance P | Sample 1347.7360 |
| Syntide 2 | Sample 1507.9324 |
| Dynorphin A Fragment 1-13 | Sample 1603.9900 |
| Renin Substrate Procine | Sample 1759.9300 |
| Big Endothelin Fragment 23-39 Bovine | Sample 1895.9616 |
| Epidermal Growth Factor Fragment 19-36 | Sample 2318.2832 |
| des-Arg1-Bradykinin | Std. 904.4670 |
| Angiotensin I Human | Std. 1296.6853 |
| Glu1-Fibrinopeptide B | Std. 1570.6670 |
| Adrenocorticotropic hormone Fragment 1-17 | Std. 2093.0867 |
| Adrenocorticotropic hormone Fragment 18-39 | Std. 2465.1990 |

The model peptides were made up as 1 µg/mL stock solutions in water and mixed in equal molar ratios so that their final concentration in the sample was 40 nM. The peptides used as mass standards were mixed with the matrix solution to a concentration of 200 nM.

Sample 2—Tryptic Digest of Mixture of 7 Proteins

Stock solutions of proteins obtained from the Sigma Chemical Co. (horse cytochrome c, horse myoglobin, human histone, bovine trypsinogen, bovine alpha-casein, human alpha-lactalbumin, bovine beta-lactoglobulin) were made up individually in water (1 mg/mL). Stock solutions of the proteins were diluted in 6 M guanidine HCl in 50 mM Tris HCl (pH 8), then reduced with 2 mM DTT for 1 hour at 65° C.

Each solution was diluted six times using Tris buffer with 1 mM $CaCl_2$, pH 7.6 and trypsin (1:20 wt/wt) and digested overnight at 37° C. After digestion, the samples were mixed in equal molar ratios (estimated equivalent protein concentration was 40 nM).

Sample 3 and 4—Yeast Lysate Digest

Yeast lysate samples were obtained from Applied Biosystems, Inc., Foster City, Calif., U.S.A., digested by trypsin (*S. cerevisiae* strain HFY1200), and separated by strong cation exchange chromatography into 23 fractions. Fraction $8^{th}$ of 23 was used as the Sample 3. The same yeast lysate sample wild type HFY1200 and yeast mutant HFY871 (upf1 deletion) was labeled with light and heavy ICAT (deuterium labeled) reagents, respectively mixed in a 1:1 molar ratio and fractionated by SCX, as described above. Fraction $10^{th}$ of 23 was used as the Sample 4.

Sample 5—Tryptic Digest of a Mixture of 5 ICAT Labeled Proteins

Proteins: β-galactosidase, lysozyme, β-lactoglobulin, ovalbumin, BSA labeled with cICAT according to the standard protocol, mixted in ratios from 1/10 to 10/1 and digested with trypsin.

The preceding discussion described the structure and operation of the improved system and method of analyzing a multi-dimensional data set for noise reduction and peak picking based on matched filtration in the chromatographic time domain. By using information about the shape and full width at half maximum (fwhm) of a chromatographic peak, as well as information about the shape and width of an MS peak and the structure of an isotopic cluster, the disclosed system and method can pick peaks with low intensities and low S/N if they have the correct peak shapes and widths in the chromatographic and m/z domains—a feature that is important for analyzing low abundant proteins. The disclosed method experimentally determines the statistics of chemical noise and random noise present in LC-MS data sets, and uses this information for improved noise reduction. The method is therefore capable of significantly improving S/N in comparison with conventional algorithms that address the problem of random noise only. Matched filtration performed by the method disclosed herein in chromatographic time domain does not distort peak shapes, even for MS peaks with low S/N. The disclosed method can filter out MS peaks corresponding to clusters of matrix ions, internal standards introduced into the matrix for calibration purposes, and products of their interactions. In addition, the disclosed method is useful for protein expression analysis by enabling the picking of a higher number of differentially expressed ICAT pairs due to increased sensitivity and mass accuracy. Extra pairs are found due to the reduction of chemical noise. For some of the pairs, the disclosed method reveals the lower intensity ICAT labeled peptide from the chemical noise and consequently recognizes the higher intensity one as a member of the ICAT pair. For others, the reduction of the chemical noise leads to a better definition of peak centroid and a more accurate determination of the distance between peaks within the ICAT pair. The noise reduction properties of the disclosed method are demonstrated for both LC-MALDI-MS and LC-ESI-MS. It should be appreciated that the system and method disclosed herein may be applied to other suitable "hyphenated" techniques such as CE-ESI-MS, CE-MALDI-MS, LC (CE)-NMR, and GC-MS.

It will further be appreciated by those of ordinary skill in the art that modifications to and variations of the above-described matched filtration with experimental noise determination for de-noising, peak picking and quantitation in LC-MS may be made without departing from the inventive concepts disclosed herein. Accordingly, the invention should not be viewed as limited except as by the scope and spirit of the appended claims.

What is claimed is:

1. A method of analyzing a multi-dimensional data set to determine the presence of one or more peaks within the data set, the peaks being representative of respective compounds, the method being performed by a computer at least one processor and at least one memory, and being used for detecting at least one constituent compound in a sample mixture, comprising the steps of:

generating a first multi-dimensional data set, the first data set being representable by a first data array including a first dimension corresponding to compound separation and a second dimension corresponding to compound characteristics;

analyzing the first data array in the compound separation dimension to generate one or more original representations of the compound separation, the original representations including one or more peaks and one or more regions having no peaks;

determining noise characteristics of the first data set based on an analysis of the regions of the original representations having no peaks;

reducing noise in the first multi-dimensional data set by performing matched filtration of the original representations of the compound separation with at least one transfer function based on the determined noise characteristics, thereby generating one or more noise-reduced representations of the compound separation, the noise-reduced representations including one or more peaks;

generating a second multi-dimensional data set with reduced noise based on the noise-reduced representations, the second data set being representable by a second data array including a compound separation dimension and a compound characteristics dimension;

analyzing the second data array in the compound separation dimension and the compound characteristics dimension to determine the presence of one or more peaks within the second data set; and in the event one or more peaks are present within the second data set, storing data indicative of the peaks within the second data set in the memory.

2. The method of claim 1 wherein the original representations of the compound separation generated in the first analyzing step and the noise-reduced representations of the compound separation generated in the noise reduction step are selected from the group consisting of an extracted ion chromatogram, an electro-chromatogram, and an electropherogram.

3. The method of claim 1 wherein the peaks representative of respective compounds are selected from the group consisting of chromatographic peaks, electro-chromatographic peaks, and electrophoretic peaks.

4. The method of claim 1 wherein the first data set generated in the first generating step and the second data set generated in the second generating step comprise respective liquid chromatography-mass spectrometry (LC-MS) data sets, the first and second LC-MS data sets being representable by respective first and second data arrays, each respective data array including a chromatographic time dimension and a mass spectral dimension, and wherein the original and noise-reduced representations of the compound separation comprise respective original and noise-reduced extracted ion chromatograms.

5. The method of claim 4 wherein the determining step includes determining the noise characteristics of the first data set, the noise characteristics being representable by a power density spectrum of the regions of the original extracted ion chromatograms having no chromatographic peaks.

6. The method of claim 5 wherein the determining step includes determining the noise characteristics of the first data set, the noise characteristics being representable by a plurality of power density spectra of respective regions of the original extracted ion chromatograms having no chromatographic peaks, and averaging the plurality of power density spectra.

7. The method of claim 5 wherein the noise reduction step includes determining at least one transfer function for matched filtration according to the equation $$H(f)=S^*(f)/P_{NN}(f),$$

$S^*(f)$ being the complex conjugate of the Fourier transform of the function representing an expected shape of the chromatographic peaks, and $P_{NN}(f)$ being a power density spectrum.

8. The method of claim 7 wherein the expected shape of the chromatographic peaks is Gaussian.

9. The method of claim 7 wherein an expected width of the chromatographic peaks is within a predetermined range of peak widths.

10. The method of claim 7 wherein the determining step includes determining at least one transfer function for matched filtration, wherein $$P_{NN}(f)=\int R_{NN}(t)\exp(-j2\pi ft)dt,$$

$R_{NN}$ being the auto-correlation function of the regions of the original extracted ion chromatograms having no chromatographic peaks.

11. The method of claim 7 wherein the noise reduction step includes performing matched filtration of the original extracted ion chromatograms for a full range of mass-to-charge (m/z) values in the mass spectral dimension of the first data array, and determining at least one transfer function for matched filtration for a predetermined number of the m/z values.

12. The method of claim 4 wherein the second analyzing step inclucles detecting peak candidates in the chromatographic time dimension for a full range of mass-to-charge (m/z) values in the mass spectral dimension, and calculating a respective peak score value for each detected peak candidate.

13. The method of claim 12 wherein the second analyzing step includes analyzing the second data array to determine the presence of one or more chromatographic peaks within the second data set based on a comparison of the calculated peak score values with the detected peak candidates.

14. The method of claim 12 wherein the calculating step includes calculating the respective peak score value for each detected peak candidate based on a plurality of criteria selected from the group consisting of the shape, the width, and the intensity of the detected peak candidate.

15. The method of claim 14 wherein the calculating step includes calculating the respective peak score value for each detected peak candidate based on at least one ratio of peak candidate intensities.

16. The method of claim 15 wherein the calculating step includes calculating each respective peak score value $Sc_f$ according to the equation $$Sc_f = Sc \cdot K_v \cdot K_I,$$

Sc being a first peak score value determined by examining the detected peak candidate in the chromatographic time dimension, and $K_v$ and $K_I$ being second and third peak score values, respectively, the second and third peak score values being determined by examining the shape of the detected peak candidate in the mass spectral dimension and by examining at least one ratio of intensities of peak candidates in at least one isotopic cluster in the mass spectral dimension.

17. The method of claim 16 further including the step of calculating the first peak score value Sc as a ratio of a maximum intensity of the noise-reduced extracted ion chromatograms to a mean intensity of the noise-reduced extracted ion chromatograms, a value of Sc greater than a first predetermined value being indicative of the presence of a peak, and a value of Sc less than a second predetermined value being indicative of the absence of peaks.

18. The method of claim 16 wherein the calculating step includes comparing each respective peak score value $Sc_f$ to a predetermined peak score threshold value $Sc_t$ to detect a first peak in each chromatogram.

19. The method of claim 18 further including the step of eliminating the first detected peak from the respective extracted ion chromatogram, and performing the noise reducing step, the second generating step, and the second analyzing step to detect a second peak in each chromatogram.

20. The method of claim 19 further including the step of repeating the eliminating step, the noise reducing step, the second generating step, and the second analyzing step a predetermined number of times equal to an expected number of peaks in each chromatogram.

21. The method of claim 4 further including comparing chromatographic elution profiles of two or more compounds of the mixture.

22. The method of claim 21 further including calculating a cross-correlationfunction ofthe noise-reduced extracted ion chromatograms corresponding to two or more co-eluting compounds of the mixture, the cross-correlation function having associated maximum arid mean values, wherein a predetermined high value of a ratio of the maximum value to the mean value is indicative of similar chromatographic elution profiles of the co-eluting compounds, thereby enabling natural isotopes or isotopically-labeled components having the same elution profile as a mono-isotopic peak to be distinguished from different components having similar elution times and different chromatographic elution profiles.

23. A method of analyzing a multi-dimensional data set to determine the presence of one or more peaks within the data set, the peaks being representative of respective compounds, the method being performed by a computer comprising at least one processor and at least one memory, and being used for detecting at least one constituent compound in a sample mixture, comprising the steps of;

generating a first multi-dimensional data set, the first data set being representable by a first data array including a first dimension corresponding to compound separation and a second dimension corresponding to compound characteristics;

analyzing the first data array in the compound separation dimension to generate one or more original representations of the compound separation, the original representations including one or more peaks;

detecting one or more peak candidates in the original representations of the compound separation;

analyzing the first data array in the compound characteristics dimension to determine the presence of one or more peaks within the first data set based on a comparison of at least one characteristic of the respective peak candidates; and in the event one or more peaks are present within the first data set, storing data indicative of the eaks within the first data set in the memory.

24. The method of claim 23 wherein the peaks representative of respective compounds are selected from the group consisting of chromatographic peaks, electro-chromatographic peaks, and electrophoretic peaks.

25. The method of claim 23 further including determining noise characteristics of the first data set based on an analysis of one or more regions of the original representations having no peaks, and reducing noise in the first data set by performing a noise reduction technique on the original representations of the compound separation based on the determined noise characteristics, thereby generating one or more noise-reduced representations of the compound separation, the noise-reduced representations including one or more peaks.

26. The method of claim 25 further including generating a second multi-dimensional data set with reduced noise based on the noise-reduced representations, the second data set being representable by a second data array including a compound separation dimension and a compound characteristics dimension, analyzing the second data array in the compound separation dimension and the compound characteristics dimension to determine the presence of at least one peak within the second data set, and in the event one or more peaks are present within the second data set, storing data indicative of the peaks within the second data set in the memory.

27. The method of claim 25 wherein the original representations of the compound separation generated in the first analyzing step and the noise-reduced representations of the compound separation generated in the noise reduction step are selected from the group consisting of an extracted ion chromatogram, an electro-chromatogram, and an electropherogram.

28. A method of quantitating a level of chromatographic peak overlapping in a tandem MS (MS/MS) mode based on the analysis of LC-MS data, the method being performed by a computer comprising at least one processor and at least one memory, and being used to increase the number of positive identifications of constituent compounds in a sample mixture, comprising the steps of:
generating a multi-dimensional data set, the data set being representable by a data array including a first dimension corresponding to compound separation and a second dimension corresponding to compound characteristics;
analyzing the data array in the compound separation dimension and the compound characteristics dimension to generate one or more representations of the compound separation, the representations including a plurality of chromatographic peaks and a plurality of MS/MS wells, each chromatographic peak being representative of a respective compound, wherein one or more of the MS/MS wells have two or more overlapping chromatographic peaks associated therewith;
identifying a plurality of overlapping chromatographic peaks in the representations of tne compound separation;
quantitating levels of overlapping for the respective overlapping chromatographic peaks;
selecting one or more of the MS/MS wells with not more than two overlapping chromatographic peaks of commensurate intensity in one well to increase the number of chromatographic peaks for positive identification; and
storing data indicative of the peaks associated with the selected MS/MS wells in the memory.

29. The method of claim 28 wherein the quantitating step includes quantitating levels of overlapping for the respective overlapping chromatographic peaks according to $$ovlp = \sum_{i=1}^{M} C_i \cdot \exp(-\Delta t_i^2 / 2\sigma_i^2) / C_0,$$

wherein M is the number of chromatographic peaks within an MS/MS window having an intensity greater a predetermined portion of a main chromatographic peak, Ci is the intensity of the overlapping chromatographic peaks, $\Delta t_i^2$ is a distance between the main chromatographic peak and the overlapping chrornatographic peak in the compound separation dimension, and $\sigma_i$ is the compound separation variance.

30. A system for analyzing a multi-dimensional data set to determine the presence of one or more peaks within the data set, the peaks being representative of respective compounds, used for detecting at least one constituent compound in a sample mixture, comprising:
a compound-separating unit configured to separate the constituent compounds in the sample mixture, and to generate data corresponding to the separated compounds;
a compound-analyzing unit configured to analyze the separated compounds and to generate data corresponding to characteristics thereof; and
a computer operative to:
generate a first multi-dimensional data set, the first data set being representable by a first data array including a first dimension corresponding to compound separation and a second dimension corresponding to compound characteristics;
analyze the first data array in the compound separation dimension to generate one or more original representations of the compound separation, the original representations including one or more peaks and one or more regions having no peaks;
determine noise characteristics of the first data set based on an analysis of the regions of the original representations having no peaks;
reduce noise in the multi-dimensional data set by performing matched filtration of the original representations of the compound separation with at least one transfer function based on the determined noise characteristics, thereby generating one or more noise-reduced representations of the compound separation, the noise-reduced representations including one or more peaks;
generate a second multi-dimensional data set with reduced noise based on the- noise-reduced representations, the second data set being representable by a second data array including a compound separation dimension and a compound characteristics dimension; and
analyze the second data array in the compound separation dimension and the compound characteristics dimension to determine the presence of one or more peaks within the second data set.

31. The system of claim 30 wherein the original and noise-reduced representations of the compound separation generated by the computer are selected from the group consisting of an extracted ion chromatogram, an electro-chromatogram, and an electropherogram.

32. The system of claim 30 wherein the peaks representative of respective compounds are selected from the group consisting of chromatographic peaks, electro-chromatographic peaks, and electrophoretic peaks.

* * * * *

UNITED STATES PATENT AND TRADEMARK OFFICE
CERTIFICATE OF CORRECTION

PATENT NO. : 7,409,298 B2
APPLICATION NO. : 10/510992
DATED : August 5, 2008
INVENTOR(S) : Victor P. Andreev It is certified that error appears in the above-identified patent and that said Letters Patent is hereby corrected as shown below:

Column 1 lines 17-19, following Statement Regarding Federally Sponsored Research or Development, line 20 "N/A" should be replaced with the following:

--This invention was made with government support under Contract No. GM15847 awarded by the National Institutes of Health.--;

Column 7, line 14, "$\leqq$" should read --$\leq$--;

Column 10, line 15, "of8." Should read --of 8.--;

Column 17, claim 7, line 12, "claim S" should read --claim 5--;

Column 17, claim 12, line 41, "inclucles" should read --includes--;

Column 18, claim 22, line 32, "cross-correlationfunction ofthe" should read --cross-correlation function of the--;

Column 18, claim 22, line 35, "arid" should read --and--;

Column 19, claim 23, line 2, "eaks" should read --peaks--;

Column 19, claim 28, line 56, "of tne" should read --of the--;

Column 20, claim 29, line 13, "chrornatographic" should read --chromatographic--; and

UNITED STATES PATENT AND TRADEMARK OFFICE
CERTIFICATE OF CORRECTION

PATENT NO.       : 7,409,298 B2
APPLICATION NO.  : 10/510992
DATED            : August 5, 2008
INVENTOR(S)      : Victor P. Andreev It is certified that error appears in the above-identified patent and that said Letters Patent is hereby corrected as shown below:

Column 20, claim 30, line 49, "the-" should read --the--.

Signed and Sealed this

Fourth Day of November, 2008

JON W. DUDAS
*Director of the United States Patent and Trademark Office*